United States Patent [19]
Hayoz et al.

[11] Patent Number: 6,013,704
[45] Date of Patent: Jan. 11, 2000

[54] HYDROXYPHENYLTRIAZINES

[75] Inventors: Pascal Hayoz, Marly, Switzerland; Andreas Valet, Binzen, Germany; Vien Van Toan, Rheinfelden, Switzerland

[73] Assignee: Ciba Specialty Chemicals Corporation, Tarrytown, N.Y.

[21] Appl. No.: 08/929,147

[22] Filed: Sep. 10, 1997

[30] Foreign Application Priority Data

Sep. 13, 1996 [CH] Switzerland ............... 2254/96

[51] Int. Cl.⁷ .................. C08K 5/3492; C07D 251/00
[52] U.S. Cl. ............... 524/100; 544/215; 544/219; 252/403
[58] Field of Search ............ 524/100; 544/215, 544/219; 252/403

[56] References Cited

U.S. PATENT DOCUMENTS

| | | | |
|---|---|---|---|
| 3,118,887 | 1/1964 | Hardy et al. | 260/248 |
| 3,242,175 | 3/1966 | Duennenberger et al. | 260/248 |
| 3,244,708 | 4/1966 | Duennenberger et al. | 260/248 |
| 3,249,608 | 5/1966 | Biland et al. | 260/248 |
| 3,843,371 | 10/1974 | Piller et al. | 96/84 |
| 4,619,956 | 10/1986 | Susi | 524/87 |
| 4,740,542 | 4/1988 | Susi | 524/87 |
| 5,229,512 | 7/1993 | Slongo et al. | 544/215 |
| 5,273,669 | 12/1993 | Schumacher et al. | 252/47.5 |
| 5,461,151 | 10/1995 | Waterman | 544/216 |
| 5,489,503 | 2/1996 | Toan | 430/507 |
| 5,543,518 | 8/1996 | Stevenson et al. | 544/215 |
| 5,648,488 | 7/1997 | Stevenson | 544/215 |

FOREIGN PATENT DOCUMENTS

| | | |
|---|---|---|
| 0356677 | 3/1990 | European Pat. Off. |
| 0434608 | 6/1991 | European Pat. Off. |
| 0444323 | 9/1991 | European Pat. Off. |
| 0483488 | 5/1992 | European Pat. Off. |
| 0704437 | 4/1996 | European Pat. Off. |
| 94/18278 | 8/1994 | WIPO |
| 9628431 | 9/1996 | WIPO |

*Primary Examiner*—Kriellion Sanders
*Attorney, Agent, or Firm*—Luther A. R. Hall; Victoria M. Malia

[57] ABSTRACT

There are described compounds of formula A

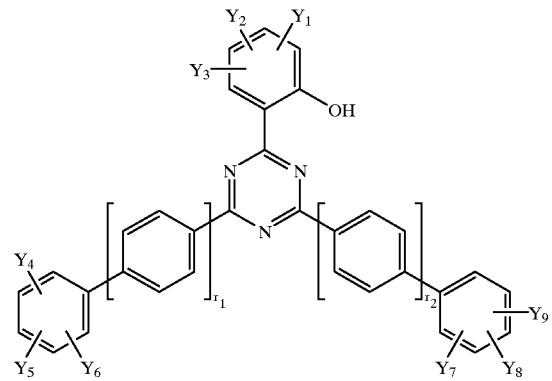

wherein $r_1$ and $r_2$ are each independently of the other 0 or 1;

$Y_1$ to $Y_9$ are each independently of the others —H, —OH, $C_1$–$C_{20}$alkyl, $C_4$–$C_{20}$cycloalkyl, $C_2$–$C_{20}$-alkenyl, $C_1$–$C_{20}$alkoxy, $C_4$–$C_{12}$cycloalkoxy, $C_2$–$C_{20}$alkenyloxy, $C_7$–$C_{20}$aralkyl, halogen, —C≡N, $C_1$–$C_5$haloalkyl, —SO₂R', —SO₃H, —SO₃M, wherein M is an alkali metal, —COOR', —CONHR', —CONR'R", —OCOOR', —OCOR', —OCONHR', (meth)acrylamino, (meth)-acryloxy, $C_6$–$C_{12}$aryl; $C_6$–$C_{12}$aryl substituted by $C_1$–$C_{12}$alkyl, $C_1$–$C_{12}$alkoxy, CN and/or by halogen; $C_3$–$C_{12}$heteroaryl; $C_3$–$C_{12}$heteroaryl substituted by $C_1$–$C_{12}$alkyl, $C_1$–$C_{12}$alkoxy, CN and/or by halogen; or Q of formula I, and at least one substituent $Y_1$ to $Y_9$ must be Q (I)

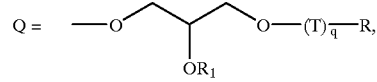

wherein q is 0 or 1,

R is a cyclic radical and $R_1$ and T are as defined in claim 1. The novel compounds are suitable, especially in combination with hindered amines, for the stabilisation of organic material against the damaging action of light, oxygen and heat.

17 Claims, No Drawings

HYDROXYPHENYLTRIAZINES

The invention relates to novel compounds of the hydroxyphenyl-s-triazine type having cyclic glycidyl ether substituents, to a synergistic stabiliser mixture comprising those compounds and compounds of the 2,2,6,6-tetramethylpiperidine type, to the use thereof in the stabilisation of organic material against damage by light, oxygen and/or heat, and to organic material stabilised by those compounds.

If it is desired to increase the light stability of an organic material, especially a coating, it is customary to add a light stabiliser. A class of light stabilisers that is very frequently used comprises UV absorbers that protect the material by absorbing the damaging radiation by means of chromophores. An important group of UV absorbers is composed of the triphenyl-s-triazines, as described inter alia in the following publications: U.S. Pat. No. 3 118 887, U.S. Pat. No. 3,242,175, U.S. Pat. No. 3,244,708, U.S. Pat. No. 3,249,608, GB-A-1 321 561, EP-A-0 434 608, U.S. Pat. No. 4,619,956, U.S. Pat. No. 5,461,151 and EP-A-0 704 437.

Stabiliser mixtures comprising UV absorbers of the tris-phenyl-s-triazine and 2,2,6,6-tetramethylpiperidine types (U.S. Pat. No. 4,619,956, U.S. Pat. No. 4,740,542, EP-A-0 444 323 and EP-A-0 483 488) have also already been proposed.

Specific compounds from the class of the tris-aryl-s-triazines have now been found that, surprisingly, have especially good stabilising properties.

The invention therefore relates to a compound of formula A

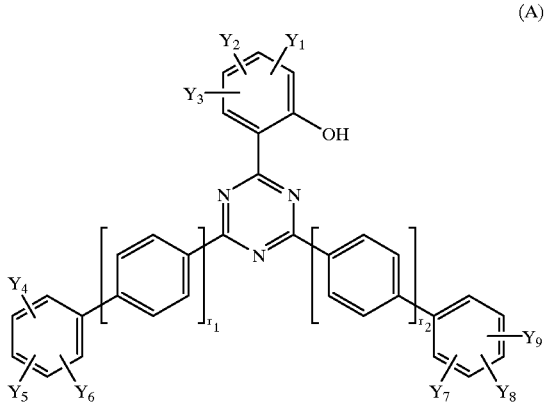

(A)

wherein $r_1$ and $r_2$ are each independently of the other 0 or 1 and the substituents $Y_1$ to $Y_9$ are each independently of the others —H, —OH, $C_1$–$C_{20}$alkyl, $C_4$–$C_{12}$-cycloalkyl, $C_2$–$C_{20}$alkenyl, $C_1$–$C_{20}$alkoxy, $C_4$–$C_{12}$cycloalkoxy, $C_2$–$C_{20}$alkenyloxy, $C_7$–$C_{20}$-aralkyl, halogen, —C≡N, $C_1$–$C_5$haloalkyl, —SO$_2$R', —SO$_3$H, —SO$_3$M, wherein M is an alkali metal, —COOR', —CONHR', —CONR'R", —OCOOR', —OCOR', —OCONHR', (meth)acrylamino, (meth)acryloxy, $C_6$–$C_{12}$aryl; $C_6$–$C_{12}$aryl substituted by $C_1$–$C_{12}$alkyl, $C_1$–$C_{12}$alkoxy, CN and/or by halogen; $C_3$–$C_{12}$heteroaryl; $C_3$–$C_{12}$heteroaryl substituted by $C_1$–$C_{12}$alkyl, $C_1$–$C_{12}$alkoxy, CN and/or by halogen; or Q of formula 1, and at least one substituent $Y_1$ to $Y_9$ must be Q

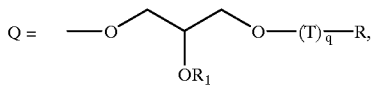

(I)

wherein q is 0 or 1, and $R_1$ is —H, $C_1$–$C_{20}$alkyl, $C_4$–$C_{12}$cycloalkyl, —COR', —COOR' or —CONHR', and T is $C_1$–$C_{20}$alkylene; $C_4$–$C_{12}$cycloalkylene; $C_1$–$C_{20}$alkylene-O—; $C_2$–$C_{50}$alkylene that is interrupted by one or more oxygen atoms and/or substituted by one or more hydroxy groups; —CO—; —SO$_2$—; phenylene; phenylene substituted by $C_1$–$C_{12}$alkyl, $C_1$–$C_{12}$alkoxy, CN and/or by halogen; biphenylene; or biphenylene substituted by $C_1$–$C_{12}$alkyl, $C_1$–$C_{12}$alkoxy, CN and/or by halogen, it being possible for T, in place of hydrogen, to be substituted by one or more substituents $R_x$ that are independent of one another, and R is $C_4$–$C_{12}$cycloalkyl, $C_4$–$C_{12}$cycloalkenyl, $C_6$–$C_{15}$bicycloalkyl, $C_6$–$C_{15}$bicycloalkenyl or $C_6$–$C_{15}$tricycloalkyl, each of which may be interrupted by one or more oxygen atoms, or is napthyl or biphenyl and, in the case where q is 1, additionally includes phenyl, it being possible for R, in place of hydrogen, to be substituted by one or more substituents $R_x$ that are independent of one another, and $R_x$ is $C_1$–$C_{20}$alkyl, $C_2$–$C_{20}$alkenyl, $C_4$–$C_{12}$cycloalkyl, $C_1$–$C_{20}$alkoxy, $C_4$–$C_{12}$cycloalkoxy, hydroxy, halogen, $C_1$–$C_5$haloalkyl, —COOR', —CONHR', —CONR'R", —OCOR', —OCOOR', —OCONHR', —NH$_2$, —NHR', —NR'R", —NHCOR', —NR"COR', —NH(meth)acryl, —O(meth)-acryl, —CN, =O, =NR'; $C_6$–$C_{12}$aryl, or $C_6$–$C_{12}$aryl substituted by $C_1$–$C_{12}$alkyl, $C_1$–$C_{12}$alkoxy, CN and/or by halogen; and R' and R" are each independently of the other —H; $C_1$–$C_{20}$alkyl; $C_4$–$C_{12}$cycloalkyl; $C_6$–$C_{12}$aryl; $C_6$–$C_{12}$aryl substituted by $C_1$–$C_{12}$alkyl, $C_1$–$C_{12}$alkoxy, CN and/or by halogen; $C_3$–$C_{12}$-heteroaryl; or $C_3$–$C_{12}$heteroaryl substituted by $C_1$–$C_{12}$alkyl, $C_1$–$C_{12}$alkoxy, CN and/or by halogen;

with the exception of the compound 2,4-bisphenyl-6-(4-[3-benzoyloxy-2-hydroxypropyloxy]-2-hydroxyphenyl)-1,3,5-triazine.

The radicals $Y_1$ to $Y_9$, $R_1$, $R_x$, R' and R" as alkyl are, within the scope of the given definitions, branched or unbranched alkyl, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl. Preferably $Y_1$ to $Y_9$, $R_1$, $R_x$, R' and R" as alkyl are short-chained, for example $C_1$–$C_8$alkyl, especially $C_1$–$C_4$alkyl, such as methyl or butyl, more especially methyl.

In the case where $r_1$ and $r_2$ are 1, $Y_4$, $Y_6$, $Y_7$ and $Y_9$ are preferably H and $Y_5$ and $Y_8$ are preferably in the p-position.

The radicals $Y_1$ to $Y_9$, R, $R_1$, $R_x$, R' and R" as $C_4$–$C_{12}$cycloalkyl are, for example, cyclobutyl, cyclopentyl, cyclohexyl, cycloheptyl, cyclooctyl, cyclononyl, cyclodecyl, cycloundecyl or cyclodocecyl. Cyclopentyl, cyclohexyl, cyclooctyl and cyclododecyl are preferred.

$C_2-C_{20}$Alkenyl includes, within the scope of the given meanings, inter alia vinyl, allyl, iso-propenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl and n-octadec-4-enyl.

$C_1-C_{20}$Alkoxy radicals are straight-chain or branched radicals, for example methoxy, ethoxy, propoxy, butoxy, pentyloxy, hexyloxy, heptyloxy, octyloxy, isooctyloxy, nonyloxy, undecyloxy, dodecyloxy, tetradecyloxy, pentadecyloxy, hexadecyloxy, heptadecyloxy, octadecyloxy, nonadecyloxy and eicosyloxy.

$C_4-C_{12}$Cycloalkoxy is, for example, cyclobutyloxy, cyclopentyloxy, cyclohexyloxy, cycloheptyloxy, cyclooctyloxy, cyclononyloxy, cyclodecyloxy, cycloundecyloxy or cyclododecyloxy, and especially cyclohexyloxy.

$C_2-C_{20}$Alkenyloxy includes, within the scope of the given meanings, inter alia vinyloxy, allyloxy, isopropenyloxy, 2-butenyloxy, 3-butenyloxy, isobutenyloxy, n-penta-2,4-dienyloxy, 3-methyl-but-2-enyloxy, n-oct-2-enyloxy, n-dodec-2-enyloxy, iso-dodecenyloxy, n-dodec-2-enyloxy or n-octadec-4-enyloxy.

$C_6-C_{12}$Aryl is generally an aromatic hydrocarbon radical, for example phenyl, biphenyl or naphthyl, and is preferably phenyl or biphenyl. That aryl may carry further substituents mentioned in the lists given herein.

Aralkyl is generally aryl-substituted alkyl; for example, $C_7-C_{20}$aralkyl includes e.g. benzyl, α-methylbenzyl, phenylethyl, phenylpropyl, phenylbutyl, phenylpentyl and phenylhexyl; benzyl and α-methylbenzyl are preferred.

A halogen substituent is —F, —Cl, —Br or —I, preferably —F or —Cl, especially —Cl.

$C_1-C_5$Haloalkyl is an alkyl radical having from 1 to 5 carbon atoms that is substituted by at least one of the afore-mentioned halogen atoms.

An alkali metal M is generally one of the metals Li, Na, K, Rb, Cs, especially Li, Na, K, more especially Na.

$C_1-C_{20}$Alkylene is, for example, methylene, ethylene, propylene, butylene, pentylene, hexylene, etc. The alkylene chain may also be branched, for example as in isopropylene.

$C_4-C_{12}$Cycloalkenyl is, for example, 2-cyclobuten-1-yl, 2-cyclopenten-1-yl, 2,4-cyclopentadien-1-yl, 2-cyclohexen-1-yl, 2-cyclohepten-1-yl or 2-cycloocten-1-yl.

$C_6-C_{15}$Bicycloalkyl is, for example, bornyl, norbornyl or 2.2.2-bicyclooctyl. Bornyl and norbornyl are preferred.

$C_6-C_{15}$Bicycloalkenyl is, for example, norbornenyl or norbornadienyl. Norbornenyl is preferred.

$C_6-C_{15}$Tricycloalkyl is, for example, 1-adamantyl or 2-adamantyl. 1-Adamantyl is preferred.

$C_3-C_{12}$Heteroaryl is preferably pyridinyl, pyrimidinyl, triazinyl, pyrrolyl, furanyl, thiophenyl or quinolinyl. That heteroaryl may carry further substituents mentioned in the lists given herein.

Special interest is accorded to a compound of formula A1

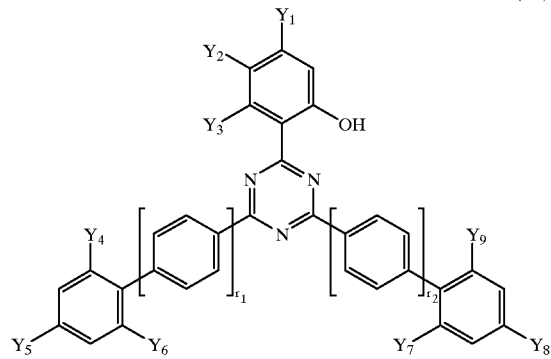

(A1)

wherein $r_1$ and $r_2$ and the substituents $Y_1$ to $Y_9$ are as defined above, especially a compound wherein $Y_1$ is Q;

$Y_2$ is H, $C_1-C_{20}$alkyl, $C_5-C_{12}$cycloalkyl, $C_7-C_{20}$aralkyl, $C_1-C_5$haloalkyl or —SO$_2$R';

$Y_3$ is H;

$Y_4$ to $Y_9$ are each independently of the others —H, —OH, $C_1-C_{20}$alkyl, $C_4-C_{12}$cycloalkyl, $C_2-C_{20}$alkenyl, $C_1-C_{20}$alkoxy, $C_4-C_{12}$cycloalkoxy, $C_2-C_{20}$alkenyloxy, $C_7-C_{20}$aralkyl, halogen, —C≡N, $C_1-C_5$haloalkyl, —SO$_2$R', —SO$_3$H, —SO$_3$M, —COOR', —CONHR', —CONR'R", —OCOOR', —OCOR', —OCONHR', (meth)acrylamino, (meth)acryloxy, $C_6-C_{12}$aryl; $C_6-C_{12}$aryl substituted by $C_1-C_{12}$alkyl, $C_1-C_{12}$alkoxy, CN and/or by halogen; $C_3-C_{12}$heteroaryl; or $C_3-C_{12}$heteroaryl substituted by $C_1-C_{12}$alkyl, $C_1-C_{12}$alkoxy, CN and/or by halogen; and $Y_5$ and $Y_8$ additionally include Q; Q being a radical of formula (I)

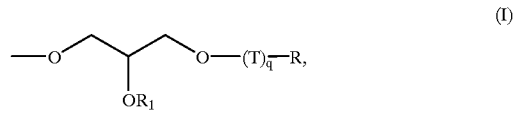

(I)

wherein q is 0 or 1, and $R_1$ is —H, $C_1-C_{20}$alkyl, $C_4-C_{12}$cycloalkyl, —COR', —COOR' or —CONHR';

T is $C_1-C_{20}$alkylene; $C_4-C_{12}$cycloalkylene; $C_1-C_{20}$alkylene-O—; $C_2-C_{50}$alkylene that is interrupted by O and/or substituted by OH; —CO—; —SO$_2$—; phenylene; or phenylene substituted by $C_1-C_{12}$alkyl, $C_1-C_{12}$alkoxy, CN and/or by halogen;

R is $C_4-C_{12}$cycloalkyl, $C_4-C_{12}$cycloalkenyl, $C_6-C_{15}$bicycloalkyl, $C_6-C_{15}$bicycloalkenyl or $C_6-C_{15}$tricycloalkyl, each of which may be interrupted by one or more oxygen atoms, or is naphthyl or biphenyl and, in the case where q is 1 and T is other than —CO—, additionally includes phenyl, it being possible for R in the said definitions to be substituted by $R_x$;

$R_x$ is $C_1-C_{12}$alkyl, $C_2-C_{20}$alkenyl, $C_1-C_4$alkoxy, $C_4-C_{12}$cycloalkoxy, hydroxy, halogen, $C_1-C_5$haloalkyl, —COOR', —CONHR', —CONR'R", —OCOR', —OCOOR', —OCONHR', —NH(meth)

acryl, —O(meth)acryl, —CN, =O, =NR'; phenyl, or phenyl substituted by $C_1$–$C_{12}$alkyl, $C_1$–$C_{12}$alkoxy, CN and/or by halogen; and R' and R" are each independently of the other $C_1$–$C_{12}$alkyl, $C_5$–$C_{12}$cycloalkyl, phenyl; or phenyl substituted by $C_1$–$C_{12}$alkyl, $C_1$–$C_{12}$alkoxy, CN and/or by halogen;

and more especially a compound wherein $r_1$ and $r_2$ are 0, $Y_4$ and $Y_7$ are each independently of the other —H, —OH, $C_1$–$C_{12}$alkyl, $C_1$–$C_{12}$alkoxy, $C_2$–$C_{20}$alkenyloxy, halogen, $C_1$–$C_5$haloalkyl or (meth)acryloxy;

$Y_5$ and $Y_8$ are each independently of the other —H, —OH, $C_1$–$C_{20}$alkyl, $C_2$–$C_{20}$alkenyl, $C_1$–$C_{20}$-alkoxy, $C_4$–$C_{12}$cycloalkoxy, $C_3$–$C_{20}$alkenyloxy, $C_7$–$C_{20}$phenylalkyl, halogen, $C_1$–$C_5$haloalkyl, —$SO_2R'$, —$SO_3H$, —$SO_3M$, —OCOOR', —OCOR', —OCONHR', (meth)acrylamino, (meth)acryloxy, phenyl; phenyl substituted by $C_1$–$C_{12}$alkyl, $C_1$–$C_{12}$alkoxy, CN and/or by halogen; or Q;

wherein in Q of formula (I)

$R_1$ is H;

T is $C_1$–$C_6$alkylene and

R is $C_4$–$C_{12}$cycloalkyl, $R_x$-substituted $C_4$–$C_{12}$cycloalkyl, phenyl, $R_x$-substituted phenyl, or $C_5$–$C_{12}$cycloalkenyl, $C_6$–$C_{15}$bicycloalkyl or $C_6$–$C_{15}$tricycloalkyl, each of which may be interrupted by one or more oxygen atoms and/or substituted by $R_x$;

$R_x$ is $C_1$–$C_4$alkyl or $C_1$–$C_4$alkoxy; and $Y_6$ and $Y_9$ are H or $C_1$–$C_{12}$alkyl.

Very special interest is accorded to a compound of formula A2

(A2)

wherein the substituent Q is as defined above.

Also of special importance is a compound of formula A3

(A3)

wherein the substituents $Q_1$ and $Q_2$ are each independently of the other as defined above for Q; very special importance is attached to compounds of formula A3 wherein the substituents $Q_1$ and $Q_2$ are identical.

Importance is also attached to a compound of formula A4

(A4)

wherein the substituents $Q_1$ to $Q_3$ are each independently of the others as defined above for Q; very special importance is attached to the compounds of formula A4 wherein the substituents $Q_1$ to $Q_3$ are identical.

Very special importance is attached to a compound of formula A5

(A5)

wherein the substituent Q is as defined above.

Special preference is given to a compound of formula A6

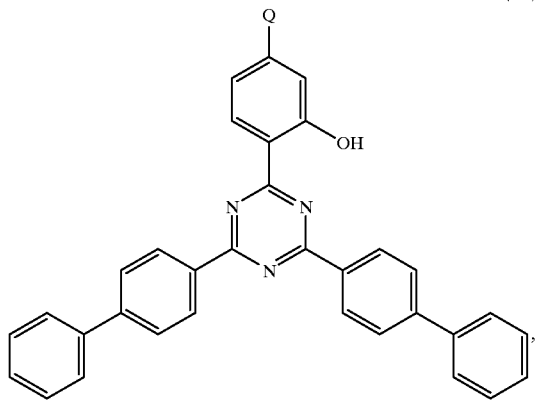

(A6)

wherein the substituent Q is as defined above.

Also preferred is a compound of formula A7

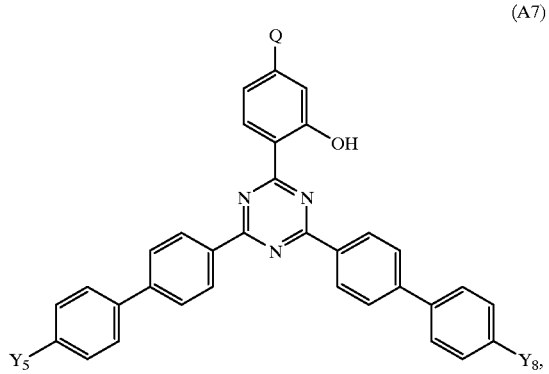

(A7)

wherein the substituents Q, $Y_5$ and $Y_8$ are as defined above.

Very special preference is given to a compound of formula A8

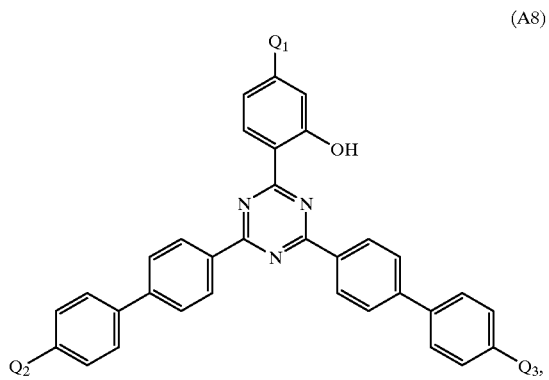

(A8)

wherein the substituents $Q_1$ to $Q_3$ are as defined above for Q; compounds of formula A8 wherein the substituents $Q_1$ to $Q_3$ are identical are especially preferred.

The invention relates also to the novel compounds of formula AII

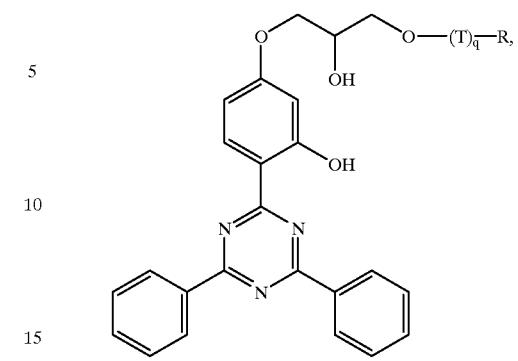

(A11)

wherein q is 0 or 1, and

T is $C_1$–$C_{20}$alkylene; $C_4$–$C_{12}$cycloalkylene; $C_1$–$C_{20}$alkylene-O—; $C_2$–$C_{50}$alkylene that is interrupted by O and/or substituted by OH; —CO—; —SO$_2$—; phenylene; or phenylene substituted by $C_1$–$C_{12}$alkyl, $C_1$–$C_{12}$alkoxy, CN and/or by halogen;

R is $C_4$–$C_{12}$cycloalkyl, $C_4$–$C_{12}$cycloalkenyl, $C_6$–$C_{15}$bicycloalkyl, $C_6$–$C_{15}$bicycloalkenyl or $C_6$–$C_{15}$tricycloalkyl, each of which may be interrupted by one or more oxygen atoms, or is naphthyl or biphenyl and, in the case where q is 1 and T is other than —CO—, additionally includes phenyl, it being possible for R in the mentioned definitions, in place of hydrogen, to be substituted by one or more substituents $R_x$ that are independent of one another, and $R_x$ is $C_1$–$C_{20}$alkyl, $C_4$–$C_{12}$cycloalkyl, $C_1$–$C_{20}$alkoxy, $C_4$–$C_{12}$cycloalkoxy, hydroxy, halogen, $C_1$–$C_5$haloalkyl, —COOH, —COOR', —CONH$_2$, —CONHR', —CONR'R", —OCOR', —OCOOR', —OCONHR', —NH$_2$, —NHR', —NR'R", —NHCOR', —NH(meth)acryl, —O(meth)acryl, —CN, =O, =NR' or (substituted) $C_6$–$C_{12}$aryl, and R' and R" are each independently of the other —H, $C_1$–$C_{20}$alkyl, $C_4$–$C_{12}$cycloalkyl, (substituted) $C_6$–$C_{12}$aryl or (substituted) $C_3$–$C_{12}$heteroaryl.

Preference is given to the compounds of formula AII wherein R is $C_4$–$C_{12}$cycloalkyl, $C_4$–$C_{12}$cycloalkenyl, $C_6$–$C_{15}$bicycloalkyl or $C_6$–$C_{15}$tricycloalkyl, each of which may be interrupted by one or more oxygen atoms, or is naphthyl or biphenyl.

Special preference is given to the compounds of formula AII wherein —T—R is benzyl, α-methylbenzyl, α-ethylbenzyl, p-methoxybenzyl, phenethyl, 2-phenylpropyl, phenpropyl, cyclododecanyl, cyclohexyl, 2-methylcyclohexyl, 3-methylcyclohexyl, 4-methylcyclohexyl, 2-tert-butylcyclohexyl, 4-tert-butylcyclohexyl, cyclohexylmethyl, 2-cyclohexylethyl, 3-cyclohexylpropyl, 2-eq.-norbornylmethyl, 4-eq.-norbornenylmethyl, bornyl, cyclopentyl, 1-adamantyl or 2-tetrahydropyranylmethyl.

Also of interest are the compounds of formula AIII

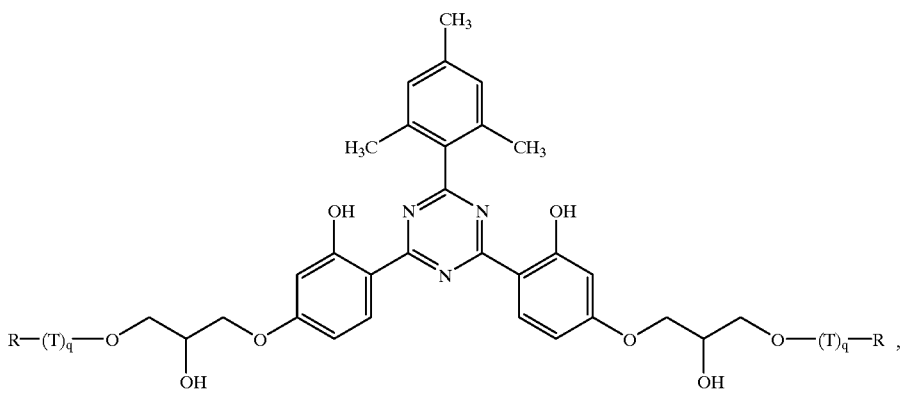

(AIII)

wherein q is 0 or 1, and

T is $C_1$–$C_{20}$alkylene; $C_4$–$C_{12}$cycloalkylene; $C_1$–$C_{20}$alkylene-O—; $C_2$–$C_{50}$alkylene that is interrupted by O and/or substituted by OH; —CO—; —$SO_2$—; phenylene; or phenylene substituted by $C_1$–$C_{12}$alkyl, $C_1$–$C_{12}$alkoxy, CN and/or by halogen, R is $C_4$–$C_{12}$cycloalkyl, $C_4$–$C_{12}$cycloalkenyl, $C_6$–$C_{15}$bicycloalkyl, $C_6$–$C_{15}$bicycloalkenyl or $C_6$–$C_{15}$tricycloalkyl, each of which may be interrupted by one or more oxygen atoms, or is naphthyl or biphenyl and, in the case where q is 1 and T is other than —CO—, additionally includes phenyl, it being possible for R in the mentioned definitions, in place of hydrogen, to be substituted by one or more substituents $R_x$ that are independent of one another, and $R_x$ is $C_1$–$C_{20}$alkyl, $C_4$–$C_{12}$cycloalkyl, $C_1$–$C_{20}$alkoxy, $C_4$–$C_{12}$cycloalkoxy, hydroxy, halogen, $C_1$–$C_5$haloalkyl, —COOH, —COOR', —$CONH_2$, —CONHR', —CONR'R", —OCOR', —OCOOR', —OCONHR', —$NH_2$, —NHR', —NR'R", —NHCOR', —NH(meth)acryl, —O(meth)acryl, —CN, =O, =NR' or (substituted) $C_6$–$C_{12}$aryl, and R' and R" are each independently of the other —H, $C_1$–$C_{20}$alkyl, $C_4$–$C_{12}$cycloalkyl, (substituted) $C_6$–$C_{12}$aryl or (substituted) $C_3$–$C_{12}$heteroaryl.

Preference is given to the compounds of formula AIII wherein R is $C_4$–$C_{12}$cycloalkyl, $C_4$–$C_{12}$cycloalkenyl, $C_6$–$C_{15}$bicycloalkyl or $C_6$–$C_{15}$tricycloalkyl, each of which may be interrupted by one or more oxygen atoms, or is naphthyl or biphenyl.

Very special preference is given to the compounds of formula AIII wherein —T—R is benzyl, α-methylbenzyl, α-ethylbenzyl, p-methoxybenzyl, phenethyl, 2-phenylpropyl, phenpropyl, cyclododecanyl, cyclohexyl, 2-methylcyclohexyl, 3-methylcyclohexyl, 4-methylcyclohexyl, 2-tert-butylcyclohexyl, 4-tert-butylcyclohexyl, cyclohexylmethyl, 2-cyclohexylethyl, 3-cyclohexylpropyl, 2-eq.-norbornylmethyl, 4-eq.-norbornenylmethyl, bornyl, cyclopentyl, 1-adamantyl or 2-tetrahydropyranylmethyl.

The invention relates also to the compounds of formula AIV

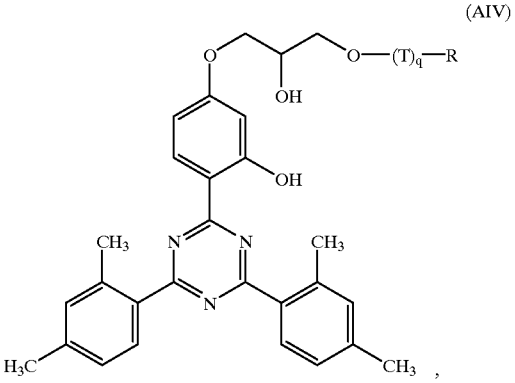

(AIV)

wherein q is 0 or 1, and

T is $C_1$–$C_{20}$alkylene; $C_4$–$C_{12}$cycloalkylene; $C_1$–$C_{20}$alkylene-O—; $C_2$–$C_{50}$alkylene that i interrupted by O and/or substituted by OH; —CO—; —$SO_2$—; phenylene; or phenylene substituted by $C_1$–$C_{12}$alkyl, $C_1$–$C_{12}$alkoxy, CN and/or by halogen;

R is $C_4$–$C_{12}$cycloalkyl, $C_4$–$C_{12}$cycloalkenyl, $C_6$–$C_{15}$bicycloalkyl, $C_6$–$C_{15}$bicycloalkenyl or $C_6$–$C_{15}$tricycloalkyl, each of which may be interrupted by one or more oxygen atoms, or is naphthyl or biphenyl and, in the case where q is 1 and T is other than —CO—, additionally includes phenyl, it being possible for R in the mentioned definitions, in place of hydrogen, to be substituted by one or more substituents $R_x$ that are independent of one another, and $R_x$ is $C_1$–$C_{20}$alkyl, $C_4$–$C_{12}$cycloalkyl, $C_1$–$C_{20}$alkoxy, $C_4$–$C_{12}$cycloalkoxy, hydroxy, halogen, $C_1$–$C_5$haloalkyl, —COOH, —COOR', —$CONH_2$, —CONHR', —CONR'R", —OCOR', —OCOOR', —OCONHR', —$NH_2$, —NHR', —NR'R", —NHCOR', —NH(meth)acryl, —O(meth)acryl, —CN, =O, =NR' or (substituted) $C_6$–$C_{12}$aryl, and R' and R" are each independently of the other —H, $C_1$–$C_{20}$alkyl, $C_4$–$C_{12}$cycloalkyl, (substituted) $C_6$–$C_{12}$aryl or (substituted) $C_3$–$C_{12}$heteroaryl.

Preference is given to the compounds of formula AIV wherein R is $C_4$–$C_{12}$cycloalkyl, $C_4$–$C_{12}$cycloalkenyl, $C_6$–$C_{15}$bicycloalkyl or $C_6$–$C_{15}$tricycloalkyl, each of which may be interrupted by one or more oxygen atoms, or is naphthyl or biphenyl.

Very special preference is given to the compounds of formula AIV wherein —T—R is benzyl, α-methylbenzyl, α-ethylbenzyl, p-methoxybenzyl, phenethyl, 2-phenylpropyl, phenpropyl, cyclododecanyl, cyclohexyl, 2-methylcyclohexyl, 3-methylcyclohexyl, 4-methylcyclohexyl, 2-tert-butylcyclohexyl, 4-tert-butylcyclohexyl, cyclohexylmethyl, 2-cyclohexylethyl, 3-cyclohexylpropyl, 2-eq.-norbornylmethyl, 4-eq.-norbornenylmethyl, bornyl, cyclopentyl, 1-adamantyl or 2-tetrahydropyranylmethyl.

The use of the compounds according to the invention in combination with hindered amines is especially advantageous. The invention therefore relates also to a synergistic stabiliser mixture comprising (a) a compound of formula A and (b) at least one 2,2,6,6-tetraalkylpiperidine derivative, or a salt thereof with any desired acid or a complex thereof with a metal.

The 2,2,6,6-tetraalkylpiperidine derivative is preferably one that contains at least one group of the formula

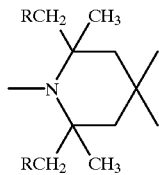

wherein R is hydrogen or methyl, especially hydrogen.

Examples of tetraalkylpiperidine derivatives that can be used may be found in EP-A-0 356 677, pages 3–17, sections a) to f). The mentioned sections of that EP-A are regarded as being part of this description. It is especially advantageous to use the compounds listed below under 2.6 or the following tetraalkylpiperidine derivatives:

bis (2,2,6,6-tetramethylpiperidin-4-yl)succinate, bis(2,2,6,6-tetramethylpiperidin-4-yl)sebacate, bis (1,2,2,6,6-pentamethylpiperidin-4-yl)sebacate, butyl-(3,5-di-tert-butyl-4-hydroxybenzyl)-malonic acid di(1,2,2,6,6-pentamethylpiperidin-4-yl) ester, bis(1-octyloxy-2,2,6,6-tetramethylpiperidin-4-yl) sebacate, tetra(2,2,6,6-tetramethylpiperidin-4-yl)butane-1,2,3,4-tetracarboxylate, tetra(1,2,2,6,6-pentamethylpiperidin-4-yl)butane-1,2,3,4-tetracarboxylate, 2,2,4,4-tetramethyl-7-oxa-3,20-diaza-21-oxo-dispiro [5.1.11.2]heneicosane, 8-acetyl-3-dodecyl-1,3,8-triaza-7,7,9,9-tetramethylspiro [4.5]decane-2,4-dione, 1,1-bis(1,2,2,6,6-pentamethylpiperidin-4-yl-oxycarbonyl)-2-(4-methoxyphenyl)-ethene, or a compound of formula

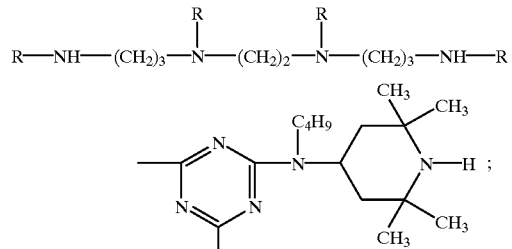

wherein R =

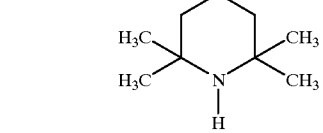

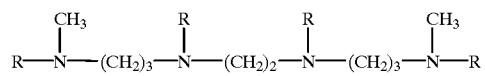

wherein R =

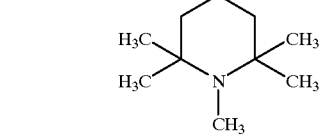

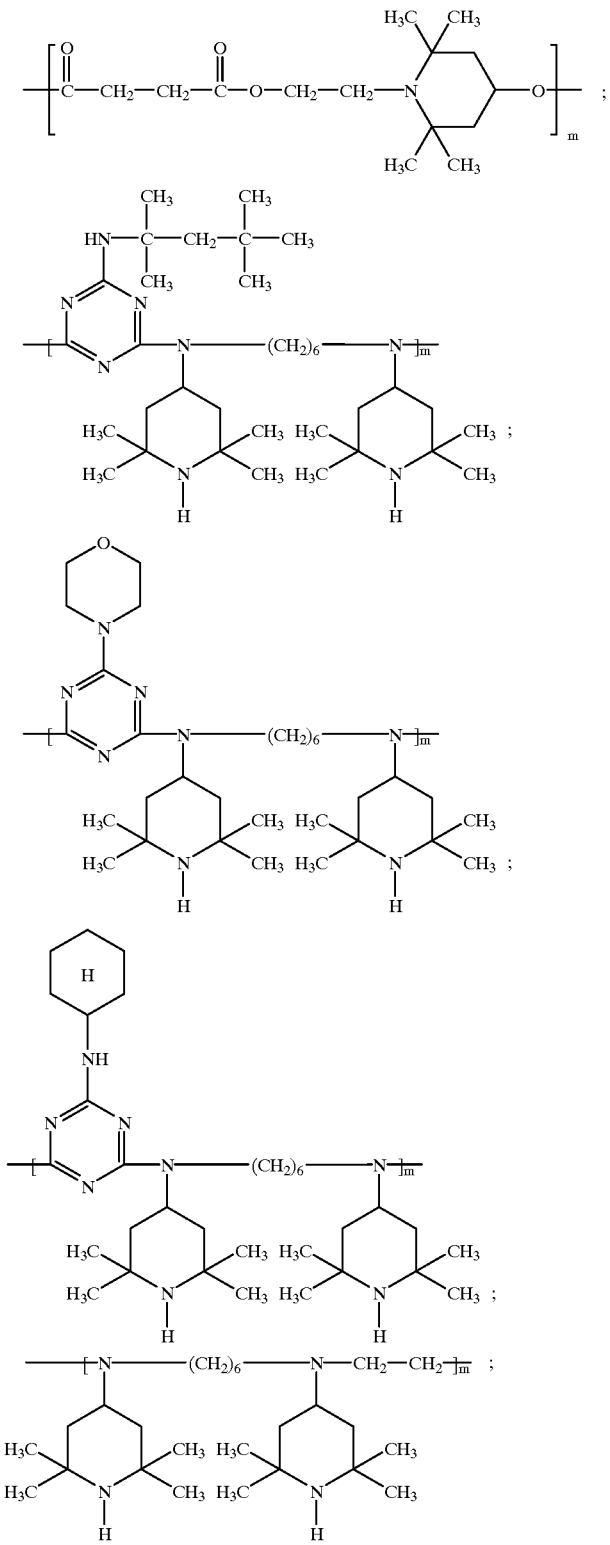

wherein m is a value from 5 to 50. Further hindered amines that can be used are described in EP-A-0 434 608 (pages 17–32).

For the preparation of, for example, the starting compound of formula IV [2-(2,4-dihydroxyphenyl)-4,6-bis(2,4-dimethylphenyl)-1,3,5-triazine], the starting materials used are, for example, commercially available halo-s-triazines which are reacted, for example in accordance with the method specified in the publication by H. Brunetti and C. E. Lüthi [Helv. Chim. Acta 55, 1566 (1972)] by Friedel-Crafts addition to corresponding phenols. The dihydroxy compound is then reacted with, for example, an alicyclic glycidyl ether (which can be prepared in a manner known per se from the corresponding hydroxy compound and epichlorohydrin) in the presence of, for example, ethyltriphenylphosphonium bromide as catalyst.

If the reaction is preferably carried out in an inert solvent, the temperature of the reaction mixture can be maintained in the boiling range (reflux) for the duration of the reaction. For that purpose, a reaction mixture containing solvent is heated to boiling point, generally under normal pressure, and the evaporated solvent is condensed with the aid of a suitable condenser and fed back into the reaction mixture.

The reactions may be carried out with the exclusion of oxygen, for example by flushing with an inert gas such as argon; oxygen is not troublesome in every case, however, so that the reaction may also be carried out without that measure.

When the reaction is complete, working-up can be carried out in accordance with customary methods; the mixture is advantageously first diluted with water, for example by adding the reaction mixture to from 1 to 4 times its volume of (ice-)water; the product can then be separated off directly or extracted; ethyl acetate or toluene, for example, are suitable for the extraction. If extraction is carried out, the product can be isolated in customary manner by removal of the solvent; this is carried out advantageously after drying of the organic phase. It is also possible to include further purification steps, for example washing with aqueous sodium hydrogen carbonate solution, dispersion of active carbon, chromatography, filtration, recrystallisation and/or distillation.

Other procedures that can be used analogously for the preparation of the compounds according to the invention are described in EP-A-434 608, page 15, line 10, to page 17, line 3, and in the Examples of that publication.

The compounds according to claim 1 are suitable especially for the stabilisation of organic materials against thermal, oxidative and actinic degradation.

Examples of such materials are:

1. Polymers of mono- and di-olefins, for example polypropylene, polyisobutylene, poly-butene-1, poly-4-methylpentene-1, polyisoprene or polybutadiene and also polymerisates of cyclo-olefins, such as, for example, of cyclopentene or norbornene; and also polyethylene (which may optionally be cross-linked), for example high density polyethylene (HDPE), low density polyethylene (LDPE), linear low density polyethylene (LLDPE), branched low density polyethylene (BLDPE).

Polyolefins, that is to say polymers of mono-olefins, as mentioned by way of example in the preceding paragraph, especially polyethylene and polypropylene, can be prepared by various processes, especially by the following methods:

a) radically (usually at high pressure and high temperature);

b) by means of catalysts, the catalyst usually containing one or more metals of group IVb, Vb, VIb or VIII. Those metals generally have one or more ligands, such as oxides, halides, alcoholates, esters, ethers, amines, alkyls, alkenyls and/or aryls, which may be either p- or s-coordinated. Those metal complexes may be free or fixed to carriers, such as, for example, to activated magnesium chloride, titanium(III) chloride, aluminium oxide or silicon oxide. Those catalysts may be soluble or insoluble in the polymerisation medium. The catalysts can be active as such in the polymerisation or further activators may be used, such as, for example, metal alkyls, metal hydrides, metal alkyl halides, metal alkyl oxides or metal alkyl oxanes, the metals being elements of group(s) Ia, IIa and/or IIIa. The activators may be modified, for example, with further ester, ether, amine or silyl ether groups. Those catalyst systems are usually known as Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of mono- and di-olefins with one another or with other vinyl monomers, such as, for example, ethylene/propylene copolymers, linear low density polyethylene (LLDPE) and mixtures thereof with low density polyethylene (LDPE), propylene/butene-1 copolymers, propylene/isobutylene copolymers, ethylene/butene-1 copolymers, ethylene/hexene copolymers, ethylene/methylpentene copolymers, ethylene/heptene copolymers, ethylene/octene copolymers, propylene/butadiene copolymers, isobutylenefisoprene copolymers, ethylene/alkyl acrylate copolymers, ethylene/alkyl methacrylate copolymers, ethylene/vinyl acetate copolymers and copolymers thereof with carbon monoxide, or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another or with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers, LLDPE-ethylene/acrylic acid copolymers and alternately or randomly structured polyalkylene-carbon monoxide copolymers and mixtures thereof with other polymers, such as, for example, polyamides.

4. Hydrocarbon resins (for example $C_5$–$C_9$) including hydrogenated modifications thereof (for example tackifier resins) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, such as, for example, styrene/butadiene, styrene/acrylonitrile, styrene/alkyl methacrylate, styrene/butadiene/alkyl acrylate and methacrylate, styrene/maleic acid anhydride, styrene/acrylonitrile/methyl acrylate; high-impact-strength mixtures consisting of styrene copolymers and another polymer, such as, for example, a polyacrylate, a diene polymer or an ethylene/propylene/diene terpolymer; and also block copolymers of styrene, such as, for example, styrene/butadiene/styrene, styrene/isoprene/styrene, styrene/ethylene-butylene/styrene or styrene/ethylene-propylene/styrene.

7. Graft copolymers of styrene or $\alpha$-methylstyrene, such as, for example, styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic acid anhydride on poly-butadiene; styrene, acrylonitrile and maleic acid anhydride or maleic acid imide on polybutadiene; styrene and maleic acid imide on polybutadiene, styrene and alkyl acrylates or alkyl methacrylates on polybutadiene, styrene and acrylonitrile on ethylene/propyleneldiene terpolymers, styrene and acrylonitrile on polyalkyl acrylates or polyalkyl methacrylates, styrene and acrylonitrile on acrylate/butadiene copolymers, and mixtures thereof with the copolymers mentioned under 6), such as those known, for example, as so-called ABS, MBS, ASA or AES polymers.

8. Halogen-containing polymers, such as, for example, polychloroprene, chlorocaoutchouc, chlorinated or chlorosulfonated polyethylene, copolymers of ethylene and chlorinated ethylene, epichlorohydrin homo- and co-polymers, especially polymers of halogen-containing vinyl compounds, such as, for example, polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.

9. Polymers derived from α,β-unsaturated acids and derivatives thereof, such as polyacrylates and polymethacrylates, or polymethyl methacrylates, polyacrylamides and polyacrylonitriles impact-resistant-modified with butyl acrylate.

10. Copolymers of the monomers mentioned under 9) with one another or with other unsaturated monomers, such as, for example, acrylonitrile/butadiene copolymers, acrylonitrile/alkyl acrylate copolymers, acrylonitrile/alkoxyalkyl acrylate copolymers, acrylonitrile/ vinyl halide copolymers or acrylonitrile/alkyl methacrylate/butadiene terpolymers.

11. Polymers derived from unsaturated alcohols and amines or their acyl derivatives or acetals, such as polyvinyl alcohol, polyvinyl acetate, stearate, benzoate or maleate, polyvinylbutyral, polyallyl phthalate, polyallylmelamine; and the copolymers thereof with olefins mentioned in Point 1.

12. Homo- and co-polymers of cyclic ethers, such as polyalkylene glycols, polyethylene oxide, polypropylene oxide or copolymers thereof with bisglycidyl ethers.

13. Polyacetals, such as polyoxymethylene, and also those polyoxymethylenes which contain comonomers such as, for example, ethylene oxide; polyacetals that are modified with thermoplastic polyurethanes, acrylates or MBS.

14. Polyphenylene oxides and sulfides and mixtures thereof with styrene polymers or polyamides.

15. Polyurethanes derived from polyethers, polyesters and polybutadienes having terminal hydroxy groups on the one hand and aliphatic or aromatic polyisocyanates on the other hand, and their initial products.

16. Polyamides and copolyamides derived from diamines and dicarboxylic acids and/or from aminocarboxylic acids or the corresponding lactams, such as polyamide 4, polyamide 6, polyamide 6,6, 6,10, 6,9, 6,12, 4,6, 12,12, polyamide 11, polyamide 12, aromatic polyamides derived from m-xylene, diamine and adipic acid; polyamides prepared from hexamethylenediamine and iso- and/or tere-phthalic acid and optionally an elastomer as modifier, for example poly-2,4,4-trimethylhexamethyleneterephthalamide or poly-m-phenyleneisophthalamide. Block copolymers of the above-mentioned polyamides with polyolefins, olefin copolymers, ionomers or chemically bonded or grafted elastomers; or with polyethers, such as, for example, with polyethylene glycol, polypropylene glycol or polytetramethylene glycol. Also polyamides or copolyamides modified with EPDM or ABS; and polyamides condensed during processing ("RIM polyamide systems").

17. Polyureas, polyimides, polyamide imides and polybenzimidazoles.

18. Polyesters derived from dicarboxylic acids and dialcohols and/or from hydroxycarboxylic acids or the corresponding lactones, such as polyethylene terephthalate, polybutylene terephthalate, poly-1 ,4-dimethylolcyclohexane terephthalate, polyhydroxybenzoates, and also block polyether esters derived from polyethers with hydroxy terminal groups; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, urea or melamine on the other hand, such as phenol-formaldehyde, urea-formaldehyde and melamine-formaldehyde resins.

22. Drying and non-drying alkyd resins.

23. Unsaturated polyester resins derived from copolyesters of saturated and unsaturated dicarboxylic acids with polyhydric alcohols, and vinyl compounds as cross-linking agents, and also the halogen-containing, not readily combustible modifications thereof.

24. Crosslinkable acrylic resins derived from substituted acrylic acid esters, such as, for example, from epoxyacrylates, urethane acrylates or polyester acrylates.

25. Alkyd resins, polyester resins and acrylate resins that are crosslinked with melamine resins, urea resins, isocyanates, isocyanurates, polyisocyanates or epoxy resins.

26. Crosslinked epoxy resins derived from polyepoxides, for example from bis-glycidyl ethers or from cycloaliphatic diepoxides.

27. Natural polymers, such as cellulose, natural rubber, gelatin, and polymer-homologously chemically modified derivatives thereof, such as cellulose acetates, propionates and butyrates, and the cellulose ethers, such as methyl cellulose; and colophonium resins and derivatives.

28. Mixtures (polyblends) of the afore-mentioned polymers, such as, for example, PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6,6 and copolymers, PA/HDPE, PA/PP, PA/PPO.

The invention therefore relates also to compositions comprising 1) an organic material susceptible to oxidative, thermal and/or actinic degradation/build-up and 2) at least one compound according to claim 1, and to the use of compounds according to claim 1 in the stabilisation of organic material against oxidative, thermal or actinic degradation/build-up.

The invention also includes a method of stabilising organic material against oxidative, thermal and/or actinic degradation/build-up, wherein at least one compound according to claim 1 is added to that material.

Special interest is accorded to the use of compounds according to claim 1 as stabilisers in synthetic organic polymers and corresponding compositions.

The organic materials to be protected are especially natural, semisynthetic or more especially synthetic organic materials. Especially preferred are synthetic organic polymers or mixtures of such polymers, especially thermoplastic polymers such as, for example, polyolefins, more especially polyethylene (PE) and polypropylene (PP). Organic materials that are likewise especially preferred are coating compositions. Coating compositions that are advantageously to be stabilised within the context of the invention are described, for example, in Ullmann's Encyclopedia of Industrial Chemistry, 5. Ed., Vol. A 18, pages 359–464, VCH Verlagsgesellschaft, Weinheim 1991.

The invention therefore relates preferably to a composition wherein the material to be protected (component 1) is a polyolefin or a surface-coating binder based on acrylic, alkyd, polyurethane, polyester or polyamide resin or correspondingly modified resins, a photographic material, a cosmetic or a sun cream.

Of special interest is the use of the compounds according to the invention as stabilisers for coatings, for example for surface coatings. The invention therefore relates also to those compositions in which component 1 is a film-forming binder.

The coating compositions according to the invention preferably contain per 100 parts by weight of solid binder (component 1) from 0.01 to 10 parts by weight, especially from 0.05 to 10 parts weight, more especially from 0.1 to 5 parts by weight, of the stabiliser according to the invention (2).

Multi-layer systems are also possible here, it being possible for the concentration of component 2 in the top layer to be higher, for example from 1 to 15 parts by weight, especially from 3 to 10 parts by weight, of component 2 per 100 parts by weight of solid binder 1.

The use of the compounds according to the invention as stabilisers in coatings provides the additional advantage that delamination, that is to say the peeling off of the coating from the substrate, is prevented. That advantage is especially useful in the case of metal substrates, and also in the case of multi-layer systems on metal substrates.

As binder (component 1) there comes into consideration in principle any binder customarily used in the art, for example those described in Ullmann's Encyclopedia of Industrial Chemistry, 5th Ed., Vol. A 18, pages 368–426, VCH Verlagsgesellschaft, Weinheim 1991. Generally, the binder will be a film-forming binder based on a thermoplastic or thermocurable resin, predominantly on a thermocurable resin. Examples thereof are alkyd, acrylic, polyester, phenol, melamine, epoxy and polyurethane resins and mixtures thereof.

Component 1 may be a cold-curable or hot-curable binder, with the addition of a curing catalyst possibly being advantageous. Suitable catalysts that accelerate the full cure of the binder are described, for example, in Ullmann's Encyclopedia of Industrial Chemistry, Vol. A 18, p. 469, VCH Verlagsgesellschaft, Weinheim 1991.

Coating compositions wherein component 1 is a binder consisting of a functional acrylate resin and a crosslinker are preferred.

Examples of coating compositions with specific binders are:

1. surface coatings based on cold- or hot-crosslinkable alkyd, acrylate, polyester, epoxy or melamine resins or mixtures of such resins, where appropriate with the addition of a curing catalyst;
2. two-component polyurethane surface coatings based on hydroxy-group-containing acrylate, polyester or polyether resins and aliphatic or aromatic isocyanates, isocyanurates or polyisocyanates;
3. one-component polyurethane surface coatings based on blocked isocyanates, isocyanurates or polyisocyanates that are deblocked during stoving;
4. one-component polyurethane surface coatings based on aliphatic or aromatic urethanes or polyurethanes and hydroxy-group-containing acrylate, polyester or polyether resins;
5. one-component polyurethane surface coatings based on aliphatic or aromatic urethane acrylates or polyurethane acrylates having free amine groups in the urethane structure and melamine resins or polyether resins, where appropriate with the addition of a curing catalyst;
6. two-component surface coatings based on (poly) ketimines and aliphatic or aromatic isocyanates, isocyanurates or polyisocyanates;
7. two-component surface coatings based on (poly) ketimines and an unsaturated acrylate resin or a polyacetoacetate resin or a methacrylamidoglycolate methyl ester;
8. two-component surface coatings based on carboxy- or amino-group-containing polyacrylates and polyepoxides;
9. two-component surface coatings based on anhydride-group-containing acrylate resins and a polyhydroxy or polyamino component;
10. two-component surface coatings based on acrylate-containing anhydrides and polyepoxides;
11. two-component surface coatings based on (poly) oxazolines and anhydride-group-containing acrylate resins or unsaturated acrylate resins or aliphatic or aromatic isocyanates, isocyanurates or polyisocyanates;
12. two-component surface coatings based on unsaturated polyacrylates and polymalonates;
13. thermoplastic polyacrylate surface coatings based on thermoplastic acrylate resins or extrinsically cross-linking acrylate resins in combination with etherified melamine resins;
14. surface-coating systems based on siloxane-modified or fluoro-modified acrylate resins.

The coating composition according to the invention preferably comprises, in addition to components 1 and 2, as a further component (3) a light stabiliser of the type of the sterically hindered amines, the 2-(2-hydroxyphenyl)-1,3,5-triazines and/or the 2-hydroxyphenyl-2H-benzotriazoles, for example as listed in the lists given below under points 2.1 and 2.8 and hereinabove. The use of the above-described synergistic mixture is of special interest. In order to achieve the maximum light stability, especially the addition of sterically hindered amines, for example those listed above, is of interest. The invention therefore relates also to a coating composition that, in addition to components 1 and 2, comprises a light stabiliser of the sterically hindered amine type as component 3.

The coating composition according to the invention also preferably comprises as further component a light stabiliser of the type of the 2-hydroxyphenyl-2H-benzotriazoles and/or 2-(2-hydroxyphenyl)-1,3,5-triazines, for example as listed in the list given below under points 2.1 and 2.8. The addition of 2-mono-resorcinyl-4,6-diaryl-1,3,5-triazines and/or 2-hydroxyphenyl-2H-benzotriazoles is of special technical interest.

Component 3 is used preferably in an amount of from 0.05 to 5 parts by weight per 100 parts by weight of the solid binder.

In addition to the components 1, 2 and optionally 3, the coating composition may comprise further components, for example solvents, pigments, colourings, plasticisers, stabilisers, thixotropic agents, drying catalysts and/or flow auxiliaries. Possible components are, for example, those described in Ullmann's Encyclopedia of Industrial Chemistry, 5th Ed., Vol. A 18, pages 429–471, VCH Verlagsgesellschaft, Weinheim 1991.

Possible drying catalysts and curing catalysts are, for example, organic metal compounds, amines, amino-group-containing resins and/or phosphines. Organic metal compounds are, for example, metal carboxylates, especially those of the metals Pb, Mn, Co, Zn, Zr or Cu, or metal chelates, especially those of the metals Al, Ti or Zr or organometal compounds such as, for example, organotin compounds.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethylacetyl acetate, salicylaldehyde, salicylaldoxime, o-hydroxyacetophenone or ethyl-trifluoroacetyl acetate and the alkanolates of those metals.

Examples of organotin compounds are dibutyltin oxide, dibutyltin dilaurate and dibutyltin dioctanoate.

Examples of amines are especially tertiary amines, for example tributylamine, triethanolamine, N-methyl-diethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride.

Amino-group-containing resins are binders and curing catalysts simultaneously. Examples thereof are amino-group-containing acrylate copolymers.

It is also possible to use phosphines, for example triphenylphosphine, as curing catalyst.

The coating compositions according to the invention may be radiation-curable coating compositions. In that case the binder consists essentially of monomeric or oligomeric compounds having ethylenically unsaturated bonds (prepolymers) which are cured, that is to say converted into a crosslinked, high-molecular-weight form, by actinic radiation after application. A UV-curing system will generally additionally contain a photoinitiator. Such systems are described in the above-mentioned publication, Ullmann's Encyclopedia of Industrial Chemistry, 5th Ed., Vol. A 18, pages 451–453. In radiation-curable coating compositions it is possible to use the stabilisers according to the invention also without the addition of sterically hindered amines.

The coating compositions according to the invention may be applied to any desired substrates, for example to metal, wood, plastics or ceramic materials. They are used especially as finishing lacquers in the surface coating of motor vehicles. When the finishing lacquer consists of two layers, the lower layer of which is pigmented and the upper layer of which is not pigmented, the coating composition according to the invention can be used for the upper or the lower layer or for both layers, but preferably for the upper layer.

The coating compositions according to the invention can be applied to the substrates by customary procedures, for example by painting, spraying, pouring, immersion or electrophoresis; see also Ullmann's Encyclopedia of Industrial Chemistry, 5th Ed., Vol. A 18, pages 491–500.

The curing of the coatings can be carried out at room temperature or with heating, depending upon the binder system used. The coatings are preferably cured at 50–150° C., or at higher temperatures in the case of powder coating compositions.

The coatings obtained according to the invention have excellent stability with respect to the damaging effects of light, oxygen and heat; special emphasis should be given to the good stability towards light and weathering of the coatings, for example surface coatings, so obtained.

The invention therefore relates also to a coating, especially a surface coating, that has been stabilised against the damaging effects of light, oxygen and heat by the addition of at least one compound according to the invention. The surface coating is preferably a finishing lacquer for motor vehicles. The invention relates also to a method of stabilising a coating based on organic polymers against damage by light, oxygen and/or heat, which method comprises combining the coating composition with at least one compound according to the invention, and to the use of the compounds according to the invention in coating compositions as stabilisers against damage by light, oxygen and/or heat.

The coating compositions may comprise an organic solvent or solvent mixture in which the binder is soluble. The coating composition may, however, alternatively be an aqueous solution or dispersion. The vehicle may also be a mixture of an organic solvent and water. The coating composition may also be a high-solids surface coating or may be solventless (e.g. powder coating composition). Powder coating compositions are, for example, those described in Ullmann's Encyclopedia of Industrial Chemistry, 5th Ed., A 18, pages 438–444. The powder coating composition may also be in the form of a powder slurry, that is to say a dispersion of the powder, preferably in water.

The pigments may be inorganic, organic or metallic pigments. The coating compositions according to the invention preferably do not contain pigments and are used as clear lacquers.

Also preferred is the use of the coating composition as a finishing lacquer for applications in the automobile industry, especially as a pigmented or non-pigmented top layer of the surface-coating. It can, however, also be used for underlying layers.

The novel UV absorbers are also suitable as light stabilisers in cosmetic preparations and sun creams. According to the invention, such preparations comprise at least one compound of the general formula (A) as well as cosmetically tolerable carriers or excipients.

For cosmetic use the light stabilisers according to the invention usually have an average particle size in the range of from 0.02 to $2\mu$, preferably from 0.05 to $1.5\mu$, and more especially from 0.1 to $1.0\mu$. The insoluble UV absorbers according to the invention can be brought to the desired particle size by customary methods, for example grinding using, for example, an extrusion mill, ball mill, vibrating mill or hammer mill. The grinding is preferably carried out in the presence of from 0.1 to 30% by weight, preferably from 0.5 to 15% by weight, based on the UV absorber, of a grinding aid, for example an alkylated vinylpyrrolidone polymer, a vinyl pyrrolidone/vinyl acetate copolymer, an acylglutamate or especially a phospholipid.

The cosmetic preparations may also comprise, in addition to the UV absorbers according to the invention, one or more further UV absorbers, for example oxanilides, triazoles, vinyl-group-containing amides or cinnamic acid amides.

Suitable oxanilides are, for example, compounds of formula

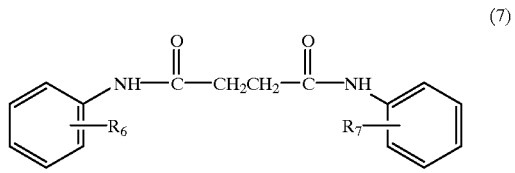

(7)

wherein $R_6$ and $R_7$ are each independently of the other $C_1$–$C_{18}$alkyl or $C_1$–$C_{18}$alkoxy.

Preferred triazole compounds correspond to formula

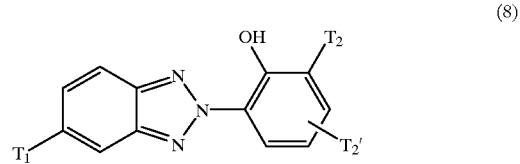

(8)

wherein $T_1$ is H, $C_1$–$C_{18}$alkyl, Cl or $OCH_3$, preferably hydrogen, and $T_2$ and $T'_2$ are each independently of the other $C_1$–$C_{18}$alkyl that is unsubstituted or substituted by a phenyl group.

A further class of triazole compounds corresponds to formula

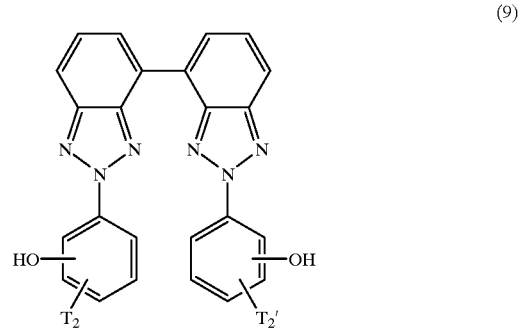

(9)

wherein $T_2$ and $T_2'$ are as defined for formula (8).

Preferred vinyl-group-containing amides correspond to formula

$R_9$—$(Y)_n$—C(=O)—C($R_{10}$)=C($R_{11}$)—N($R_{12}$)($R_{13}$), (10)

wherein $R_9$ is $C_1$–$C_{18}$alkyl, preferably $C_1$–$C_5$alkyl or phenyl, wherein phenyl may be substituted by two or three substituents selected from hydroxy, $C_1$–$C_{18}$alkyl and $C_1$–$C_{18}$alkoxy and a —C(=O)—$OR_8$— group wherein $R_8$ is $C_1$–$C_{18}$alkyl;

$R_{10}$, $R_{11}$, $R_{12}$ and $R_{13}$ are each independently of the others hydrogen or $C_1$–$C_{18}$alkyl;

Y is N or O; and n is 0 or 1.

Preferred cinnamic acid derivatives correspond to formula

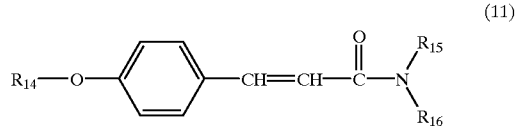

(11)

wherein $R_{14}$ is hydroxy or $C_1$–$C_4$alkoxy, preferably methoxy or ethoxy;

$R_{15}$ is hydrogen or $C_1$–$C_4$alkyl, preferably methyl or ethyl;

$R_{16}$ is —(CONH)$_n$-phenyl and the phenyl ring may be substituted by one, two or three substituents selected from OH, $C_1$–$C_{18}$-alkyl and $C_1$–$C_{18}$alkoxy and a —C(=O)—$OR_8$ group, wherein $R_8$ is as defined above.

The additional UV absorbers, used in addition to the UV absorbers according to the invention, are known, for example, from Cosmetics & Toiletries (107), 50ff (1992).

The cosmetic composition according to the invention contains from 0.1 to 15% by weight, preferably from 0.5 to 10% by weight, based on the total weight of the composition, of a UV absorber or of a mixture of UV absorbers and a cosmetically tolerable excipient.

The cosmetic composition can be prepared by physically mixing the UV absorber(s) with the excipient by customary methods, for example by simply stirring the two materials together.

The cosmetic composition according to the invention can be formulated as a water-in-oil or oil-in-water emulsion, as an oil-in-oil-alcohol lotion, as a vesicular dispersion of an ionic or non-ionic amphiphilic lipid, as a gel, a solid stick or as an aerosol formulation.

As a water-in-oil or oil-in-water emulsion, the cosmetically tolerable excipient preferably contains from 5 to 50% of an oil phase, from 5 to 20% of an emulsifier and from 30 to 90% water. The oil phase may comprise any oil suitable for cosmetic formulations, for example one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

For the cosmetic formulations according to the invention it is possible to use any conventionally usable emulsifier, such as, for example, one or more ethoxylated esters of natural derivatives, for example polyethoxylated esters of hydrogenated castor oil; or a silicone oil emulsifier, for example silicone polyol; an optionally ethoxylated fatty acid soap; an ethoxylated fatty alcohol; an optionally ethoxylated sorbitan ester; an ethoxylated fatty acid; or an ethoxylated glyceride.

The cosmetic formulation may also comprise other components, for example emollients, emulsion stabilisers, skin humectants, skin tanning accelerators, thickeners, for example Xanthan, moisture-retention agents, for example glycerol, preservatives, perfumes and colourings.

The cosmetic formulations according to the invention are distinguished by excellent protection of human skin against the damaging effect of sunlight with at the same time safe tanning of the skin. Furthermore, the cosmetic preparations according to the invention are water-resistant when applied to the skin.

Further materials to be stabilised using the compounds according to the invention are photographic materials. Such materials include especially those described in Research Disclosure 1990, 31429 (pages 474–480) for photographic reproduction and other reproduction techniques.

In general, the compounds according to claim 1 are added to the material to be stabilised in amounts of from 0.01 to 10%, preferably from 0.01 to 5%, especially from 0.01 to 2%, based on the total weight of the stabilised composition. The use of the compounds according to the invention in amounts of from 0.05 to 1.5%, especially from 0.1 to 0.5%, is especially preferred.

Incorporation into the materials can be effected, for example, by mixing in or applying the compounds according to claim 1 and optionally further additives in accordance with the methods customary in the art. In the case of polymers, especially synthetic polymers, the incorporation can take place before or during shaping, or by application of the dissolved or dispersed compound to the polymer, optionally with subsequent evaporation of the solvent. In the case of elastomers, they can be stabilised also in the form of latices. A further possible method of incorporating the compounds according to claim 1 into polymers is their addition before, during or immediately after the polymerisation of the corresponding monomers or before crosslinking. In that case the compounds according to claim 1 can be used as such but they may also be added in encapsulated form (for example in waxes, oils or polymers). In the case of addition before or during polymerisation, the compounds according to claim 1 can also act as regulators for the chain length of the polymers (chain terminators).

The compounds according to claim 1 can also be added to the plastics materials to be stabilised in the form of a master batch, which contains the compound, for example, in a concentration of from 2.5 to 25% by weight.

The compounds according to claim 1 can advantageously be incorporated in accordance with the following methods:

as an emulsion or dispersion (for example to latices or emulsion polymers);

as a dry mixture during the mixing of additional components or polymer mixtures;

by direct addition into the processing apparatus (for example extruder, kneader, etc.);

as a solution or melt.

Polymer compositions according to the invention can be used in various forms or processed to form a variety of products, for example they may be used as (or processed to form) films, fibres, small strips, moulding compounds, shaped pieces, or as binders for surface coatings, adhesives or cements.

In addition to the compounds according to claim 1, the compositions according to the invention may also contain, as additional component (3), one or more conventional additives, for example the following:

1. Anti-oxidants 1.1. Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-di-octadecyl-4-methylphenol, 2,4,6-tricyclohexylphenol, 2,6-di-tert-butyl-4-methoxymethylphenol, nonylphenols that are linear or are branched in the side chain, for example 2,6-di-nonyl-4- methylphenol, 2,4-dimethyl-6-(1'-methyl-undec-1'-yl)-phenol, 2,4-dimethyl-6-(1'-methyl-heptadec-1'-yl)-phenol, 2,4-dimethyl-6-(1'-methyl-tridec-1'-yl)-phenol and mixtures thereof.

1.2. Alkylthiomethylphenols, for example 2,4-di-octylthiomethyl-6-tert-butylphenol, 2,4-di-octylthiomethyl-6-methylphenol, 2,4-di-octylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butyl-hydroquinone, 2,5-di-tert-amyl-hydroquinone, 2,6-diphenyl-4-octadecyloxyphenol, 2,6-di-tert-butyl-hydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thio-bis(6-tert-butyl-4-methylphenol), 2,2'-thio-bis(4-octylphenol), 4,4'-thio-bis(6-tert-butyl-3-methylphenol), 4,4'-thio-bis(6-tert-butyl-2-methylphenol), 4,4'-thio-bis(3,6-di-sec-amylphenol), 4,4'-bis(2,6-dimethyl-4-hydroxyphenyl) disulfide.

1.6. Alkylidene bisphenols, for example 2,2'-methylene-bis(6-tert-butyl-4-methylphenol), 2,2'-methylene-bis(6-tert-butyl-4-ethylphenol), 2,2'-methylene-bis[4-methyl-6-(α-methylcyclohexyl)-phenol], 2,2'-methylene-bis(4-methyl-6-cyclohexylphenol), 2,2'-methylene-bis(6-nonyl-4-methylphenol), 2,2'-methylene-bis(4,6-di-tert-butylphenol), 2,2'-ethylidene-bis(4,6-di-tert-butylphenol), 2,2'-ethylidene-bis(6-tert-butyl-4-isobutylphenol), 2,2'-methylene-bis[6-(α-methylbenzyl)-4-nonylphenol], 2,2'-methylene-bis[6-(α,α-dimethylbenzyl)-4-nonylphenol], 4,4'-methylene-bis(2,6-di-tert-butylphenol), 4,4'-methylene-bis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methylphenyl) dicyclopentadiene, bis[2-(3'-tert-butyl-2'-hydroxy-5'-methyl-benzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercapto-butane, 1,1,5,5-tetra(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzyl-mercaptoacetate, tridecyl-4-hydroxy-3,5-di-tert-butylbenzyl-mercaptoacetate, tris(3,5-di-tert-butyl-4-hydroxybenzyl)-amine, bis(4-tert-butyl-3-hydroxy-2,6-dimethylbenzyl) dithioterephthalate, bis(3,5-di-tert-butyl-4-hydroxybenzyl) sulfide, isooctyl-3,5-di-tert-butyl-4-hydroxybenzyl-mercaptoacetate.

1.8. Hydroxybenzylated malonates, for example dioctadecyl-2,2-bis(3,5-di-tert-butyl-2-hydroxybenzyl) malonate, di-octadecyl-2-(3-tert-butyl-4-hydroxy-5-methylbenzyl)malonate, di-dodecylmercaptoethyl-2,2-bis (3,5-di-tert-butyl-4-hydroxybenzyl)malonate, di[4-(1,1,3,3-tetramethylbutyl)phenyl]-2,2-bis(3,5-di-tert-butyl-4-hydroxybenzyl)malonate.

1.9. Hydroxybenzyl aromatic compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis-octylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzyl phosphonate, diethyl-3,5-di-tert-butyl-4-hydroxybenzyl phosphonate, dioctadecyl-3,5-di-tert-butyl-4-hydroxybenzyl phosphonate, dioctadecyl-5-tert-butyl-4-hydroxy-3-methylbenzyl phosphonate, calcium salt of 3,5-di-tert-butyl-4-hydroxybenzylphosphonic acid monoethyl ester.

1.12. Acylaminophenols, for example 4-hydroxylauric acid anilide, 4-hydroxystearic acid anilide, N-(3,5-di-tert-butyl-4-hydroxyphenyl)carbamic acid octyl ester.

1.13. Esters of β-(3,5-di-tert-butyl-4-hydroxyphenyl) propionic acid with mono- or poly-hydric alcohols, such as, for example, with methanol, ethanol, n-octanol, iso-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)-isocyanurate, N,N'-bis(hydroxyethyl) oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or poly-hydric alcohols, such as, for example, with methanol, ethanol, n-octanol, iso-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)-isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or poly-hydric alcohols, such as, for example, with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenylacetic acid with mono- or poly-hydric alcohols, such as, for example, with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)-isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid, such as, for example, N, N'-bis(3,5-di-tert-butyl-4-hydroxyphenylpropionyl) hexamethylenediamine, N, N'-bis (3,5-di-tert-butyl-4-hydroxyphenylpropionyl) trimethylenediamine, N,N'-bis(3,5-di-tert-butyl-4-hydroxyphenylpropionyl)hydrazine.

1.18. Ascorbic acid (Vitamin C).

1.19. Aminic antioxidants, such as, for example, N,N'-di-isopropyl-p-phenylenediamine, N,N'-di-sec-butyl-p- phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di(naphthyl-2)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylamino-phenol, 4-nonanoylaminophenol, 4-dodecanoylamino-phenol, 4-octadecanoylamino-phenol, di(4-methoxyphenyl)-amine, 2,6-di-tert-butyl-4-dimethylamino-methyl-phenol, 2,4'-diamino-diphenylmethane, 4,4'-diamino-diphenylmethane, N,N,N',N'-tetramethyl-4,4'-diamino-diphenylmethane, 1,2-di[(2-methyl-phenyl)-amino]ethane, 1,2-di(phenylamino) propane, (o-tolyl)-biguanide, di[4-(1',3'-dimethyl-butyl)-phenyl]amine, tert-octylated N-phenyl-1-naphthylamine, mixture of mono- and di-alkylated tert-butyl-/tert-octyl-diphenylamines, mixture of mono- and di-alkylated nonyldiphenylamines, mixture of mono- and di-alkylated dodecyidiphenylamines, mixture of mono- and di-alkylated isopropyl-/isohexyl-diphenylamines, mixtures of mono- and di-alkylated tert-butyldiphenylamines, 2,3-dihydro-3,3-dimethyl-4H-1,4-benzothiazines, phenothiazine, mixture of mono- and di-alkylated tert-butyl-/tert-octyl-phenothiazines, mixture of mono- and di-alkylated tert-octyl-phenothiazines, N-allylphenothiazine, N,N,N',N'-tetraphenyl-1,4-diaminobut-2-ene, N,N-bis(2,2,6,6-tetramethyl-piperidin-4-yl)-hexamethylenediamine, bis(2,2,6,6-tetramethylpiperidin-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)-benzotriazoles, such as, for example, 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)phenyl)-benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis(α,α-dimethylbenzyl)-2'-hydroxyphenyl)-benzotriazole, mixture of 2-(3'-tert-butyl-2'-hydroxy-5'-(2-octyloxycarbonylethyl) phenyl)-5-chlorobenzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)-benzotriazole, 2-(3'-dodecyl-2'-hydroxy-5'-methylphenyl)-benzotriazole, and 2-(3'-tert-butyl-2'-hydroxy-5'-(2-isooctyloxycarbonylethyl)phenyl-benzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl]-benzotriazole with polyethylene glycol 300; R—CH$_2$CH$_2$—COO—(CH$_2$)$_6$—OCO—CH$_2$CH$_2$—R in which R=3'-tert-butyl-4'-hydroxy-5'-2H-benzotriazol-2-yl-phenyl; 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]-benzotriazole.

2.2. 2-Hydroxybenzophenones, such as, for example, the 4-hydroxy, 4-methoxy, 4-octyloxy, 4-decyloxy, 4-dodecyloxy, 4-benzyloxy, 4,2',4'-trihydroxy, 2'-hydroxy-4,4'-dimethoxy derivative.

2.3. Esters of unsubstituted or substituted benzoic acids, such as, for example, 4-tert-butylphenylsalicylate, phenylsalicylate, octylphenylsalicylate, dibenzoylresorcinol, bis(4-tert-butylbenzoyl)resorcinol, benzoylresorcinol, 3,5-di-tert-butyl-4-hydroxybenzoic acid 2,4-di-tert-butyl-phenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.

2.4. Acrylates, such as, for example, α-cyano-β,β-diphenylacrylic acid ethyl ester or isooctyl ester, α-methoxycarbonyl-cinnamic acid methyl ester, α-cyano-β-methyl-p-methoxy-cinnamic acid methyl ester or butyl ester, α-methoxycarbonyl-p-methoxy-cinnamic acid methyl ester, N-(β-methoxycarbonyl-β-cyanovinyl)-2-methyl-indoline.

2.5. Nickel compounds, such as, for example, nickel complexes of 2,2'-thio-bis[4-(1,1,3,3-tetramethylbutyl) phenol], such as the 1:1 or 1:2 complex, optionally with additional ligands, such as n-butylamine, triethanolamine or N-cyclohexyl-diethanolamine, nickel dibutyl dithiocarbamate, nickel salts of 4-hydroxy-3,5-di-tert-butylbenzylphosphonic acid monoalkyl esters, such as of the methyl or ethyl ester, nickel complexes of ketoximes, such as of 2-hydroxy-4-methylphenylundecyl ketoxime, nickel complexes of 1-phenyl-4-lauroyl-5-hydroxypyrazole, optionally with additional ligands.

2.6. Further sterically hindered amines, such as, for example, bis(2,2,6,6-tetramethylpiperidin-4-yl)sebacate, bis (2,2,6,6-tetramethyl-piperidin-4-yl)succinate, bis(1,2,2,6,6-pentamethylpiperidin-4-yl)sebacate, bis(1-octyloxy-2,2,6,6-tetramethylpiperldin-4-yl)-sebacate, n-butyl-3,5-di-tert-butyl-4-hydroxybenzyl-malonic acid bis(1,2,2,6,6-pentamethylpiperidyl) ester, condensation product of 1-hydroxyethyl-2,2,6,6-tetramethyl-4-hydroxypiperidine and succinic acid, condensation product of N,N'-bis(2,2,6,6-tetramethyl-4-piperidyl)-hexamethylenediamine and 4-tert-octylamino-2,6-dichloro-1,3,5-s-triazine, tris-(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis-(1,2,2,6,6-pentamethylpipeeidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, condensation product of N,N'-bis(2,2,6,6-tetramethyl-4-piperidyl) hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)-pyrrolidine-2,5-dione, 3-dodecyl-1-(1,2,2,6,6-pentamethyl-4-piperidyl)-pyrrolidine-2,5-dione, mixture of 4-hexadecyloxy- and 4-stearyloxy-2,2,6,6-tetramethylpiperidine, condensation product of N,N'-bis(2,2,6,6-tetramethyl-4-piperidyl) hexamethylendiamine and 4-cyclohexylamino-2,6-dichloro- 1,3,5-triazine, condensation product of 1,2-bis(3-aminopropylamino)-ethane and 2,4,6-trichloro-1,3,5-triazine and also 4-butylamino-2,2,6,6-tetramethyl-piperidine (CAS Reg. No. [136504-96-6]); N-(2,2,6,6-tetramethyl-4-piperidyl)-n-dodecylsuccinimide, N-(1,2,2,6, 6-pentamethyl-4-piperidyl)-n-dodecylsuccinimide, 2-undecyl-7,7,9,9-tetramethyl-1-oxa-3,8-diaza-4-oxo-spiro [4.5]decane, reaction product of 7,7,9,9-tetramethyl-2-cycloundecyl-1-oxa-3,8-diaza-4-oxospiro[4.5]decane and epichlorohydrin.

2.7. Oxalic acid diamides, such as, for example, 4,4'-di-octyloxy-oxanilide, 2,2'-diethoxyoxanilide, 2,2'-di-octyloxy-5,5'-di-tert-butyl-oxanilide, 2,2'-di-dodecyloxy-5, 5'-di-tert-butyloxanilide, 2-ethoxy-2'-ethyl-oxanilide, N,N'-bis(3-dimethylaminopropyl)oxalamide, 2-ethoxy-5-tert-butyl-2'-ethyloxanilide and a mixture thereof with 2-ethoxy-2'-ethyl-5,4'-di-tert-butyloxanilide, mixtures of o- and p-methoxy- and also of o- and p-ethoxy-di-substituted oxanilides.

2.8. 2-(2-Hydroxyphenyl)-1,3,5-triazines, such as, for example, 2,4,6-tris(2-hydroxy-4-octyl-oxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4, 6-bis(2,4-dimethylphenyl)-1,3,5-triazine, 2,4-bis(2-hydroxy-4-propyloxyphenyl)-6-(2,4-dimethylphenyl)-1,3, 5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethylphenyl)-1,3,5-triazine, 2-[2-hydroxy-4-(2-hydroxy-3-octyloxy-propyloxy)-phenyl]-4,6-bis(2,4-dimethylphenyl)-1,3,5-triazine, 2-[4-(dodecyloxy/tridecyloxy-2-hydroxypropoxy)-2-hydroxy-phenyl]-4,6-bis (2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,6-triazine, 2-(2-hydroxyphenyl)-4-(4-methoxyphenyl)-6-phenyl-1,3,5-triazine.

3. Metal deactivators, such as, for example, N,N'-diphenyloxalic acid diamide, N-salicylal-N'-salicyloylhydrazine, N,N'-bis(salicyloyl)hydrazine, N,N'-bis (3,5-di-tert-butyl-4-hydroxyphenylpropionyl)hydrazine, 3-salicyloylamino-1,2,4-triazole, bis(benzylidene)oxalic acid dihydrazide, oxanilide, isophthalic acid dihydrazide, sebacic acid bis-phenylhydrazide, N,N'-diacetyl-adipic acid dihydrazide, N,N'-bis-salicyloyl-oxalic acid dihydrazide, N,N'-bis-salicyloyl-thiopropionic acid dihydrazide.

4. Phosphites and Dhosphonites, such as, for example, triphenylphosphite, diphenylalkylphosphites, phenyldialkylphosphites, tris(nonylphenyl)phosphite, trilaurylphosphite, trioctadecylphosphite, distearyl-pentaerythritol diphosphite, tris(2,4-di-tert-butylphenyl) phosphite, diisodecylpentaerythritol diphosphite, bis(2,4-di-tert-butylphenyl)pentaerythritol diphosphite, bis(2,6-di-tert-butyl-4-methylphenyl)pentaerythritol diphosphite, bis-isodecyloxy-pentaerythritol diphosphite, bis(2,4-di-tert-butyl-6-methylphenyl)pentaerythritol diphosphite, bis-(2,4, 6-tri-tert-butylphenyl)pentaerythritol diphosphite, tristearyl-sorbitol triphosphite, tetrakis-(2,4-di-tert-butylphenyl)-4,4'-biphenylene-diphosphonite, 6-isooctyloxy-2,4,8,10-tetra-tert-butyl-12H-dibenz[d,g]-1,3,2-dioxaphosphocine, 6-fluoro-2,4,8, 10-tetra-tert-butyl-12-methyldibenz[d,g]-1, 3,2-dioxaphosphocine, bis(2,4-di-tert-butyl-6-methylphenyl)methylphosphite, bis(2,4-di-tert-butyl-6-methylphenyl)ethylphosphite.

5. Hydroxylamines, such as, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine from hydrogenated tallow fatty amines.

6. Nitrones such as, for example, N-benzyl-α-phenyl-nitrone, N-ethyl-α-methyl-nitrone, N-octyl-α-heptyl-nitrone, N-lauryl-α-undecyl-nitrone, N-tetradecyl-α-tridecyl-nitrone, N-hexadecyl-α-pentadecyl-nitrone, N-octadecyl-α-heptadecyl-nitrone, N-hexadecyl-α-heptadecylnitrone, N-octadecyl-α-pentadecyl-nitrone, N-heptadecyl-α-heptadecyl-nitrone, N-octadecyl-α-hexadecyl-nitrone, nitrones derived from N,N-dialkylhydroxylamines prepared from hydrogenated tallow fatty amines.

7. Thiosynergistic compounds, such as, for example, thiodipropionic acid dilauryl ester or thiodipropionic acid distearyl ester.

8. Peroxide-decomposing compounds, such as, for example, esters of β-thio-dipropionic acid, for example the lauryl, stearyl, myristyl or tridecyl ester, mercaptobenzimidazole, the zinc salt of 2-mercaptobenzimidazole, zinc dibutyl-dithiocarbamate, dioctadecyidisulfide, pentaerythritol tetrakis(β-dodecylmercapto)propionate.

9. Polyamide stabilisers, such as, for example, copper salts in combination with iodides and/or phosphorus compounds and salts of divalent manganese.

10. Basic co-stabilisers, such as, for example, melamine, polyvinylpyrrolidone, dicyandiamide, triallyl cyanurate, urea derivatives, hydrazine derivatives, amines, polyamides, polyurethanes, alkali metal and alkaline earth metal salts of higher fatty acids, for example calcium stearate, zinc stearate, magnesium behenate, magnesium stearate, sodium ricinoleate, potassium palmitate, antimony pyrocatecholate or tin pyrocatecholate.

11. Nucleating agents, such as, for example, inorganic substances, such as, for example, talc, metal oxides, such as titanium dioxide or magnesium oxide, phosphates, carbonates or sulfates of, preferably, alkaline earth metals; organic compounds, such as mono- or poly-carboxylic acids and their salts, such as, for example, 4-tert-butylbenzoic acid, adipic acid, diphenylacetic acid, sodium succinate or sodium benzoate; polymeric compounds, such as, for example, ionic copolymerisates ("ionomers").

12. Fillers and reinforcing agents, such as, for example, calcium carbonate, silicates, glass fibres, glass beads, asbestos, talc, kaolin, mica, barium sulfate, metal oxides and hydroxides, carbon black, graphite, sawdust, and dusts and fibres of other natural products, synthetic fibres.

13. Other additives, such as, for example, plasticisers, glidants, emulsifiers, pigments, rheology additives, catalysts, flow auxiliaries, optical brighteners, flame retardants, antistatics, propellants.

14. Benzofuranones and indolinones, as described, for example, in U.S. Pat. No. 4,325,863, U.S. Pat. No. 4,338, 244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102, or 3-[4-(2-acetoxyethoxy)phenyl]-5,7-di-tert-butyl-benzofuran-2-one, 5,7-di-tert-butyl-3-[4-(2-stearoyloxyethoxy) phenyl]-benzofuran-2-one, 3,3'-bis[5,7-di-tert-butyl-3-(4-[2-hydroxyethoxy]phenyl)-benzofuran-2-one], 5,7-di-tert-butyl-3-(4-ethoxyphenyl)benzofuran-2- one, 3-(4-acetoxy-3,5-dimethylphenyl)-5,7-di-tert-butyl-benzofuran-2-one, 3-(3,5-dimethyl-4-pivaloyloxy-phenyl)-5,7-di-tert-butyl-benzofuran-2-one.

Such additional additives are used advantageously in amounts of from 0.1 to 10% by weight, for example from 0.2 to 5% by weight, based on the polymer to be stabilised.

The following Examples further illustrate the invention. All parts and percentages, in the Examples as well as in the remainder of the description and in the patent claims, relate to weight, unless indicated to the contrary. The following abbreviations are used in the Examples and in the Tables:

AcOEt: ethyl acetate
$CHCl_3$: chloroform
DSC: Differential Scanning Calorimetry =differential thermoanalysis
$\epsilon$: molar extinction coefficient
$^1$H-NMR: nuclear magnetic resonance of the nuclide $^1$H
$T_g$: glass transition temperature

PREPARATION EXAMPLES

General Preparation Example for the cycloglycidyl ethers (Example I.18):

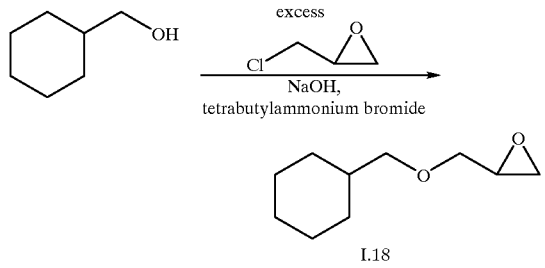

32.66 g (0.286 mol) of hydroxymethylcyclohexane, 79.4 g (0.858 mol) of epichlorohydrin and 1 g of tetrabutylammonium bromide as catalyst are placed in a vessel and stirred at room temperature. With cooling, 13.7 g (0.343 mol) of finely powdered NaOH are slowly added. Stirring is then carried out at 60° C. for 2 hours and the emulsion is then filtered over ®Hyflo [kieselguhr supplied by Celite Italiana Milan]. The filtrate is subjected to fractional distillation. Yield: 42.36 g (87% of the theoretical yield).

Analyses:

Appearance: colourless liquid, boiling point: 105–109° C./18 mm Hg $^1$H-NMR ($CDCl_3$, 300 MHz): The spectrum agrees with that expected of the product.

Empirical formula: $C_{10}H_{18}O_2$, molecular weight: 170.25 g/mol

Elemental analysis:

|   | calculated | found |
| --- | --- | --- |
| C | 70.55% | 70.35% |
| H | 10.66% | 10.69% |
| Cl | 0.00% | <0.30% |
| epoxy content | 5.87 mol/kg | 5.88 mol/kg |

General Preparation Example for the cycloglycidyl esters (Example I.26) [see in this connection: Nguyen C. Hao and Josef Mileziva in Die Angewandte Makromolekulare Chemie 31 (1973), pages 83–113, especially pages 87, 88 and 94, 95]:

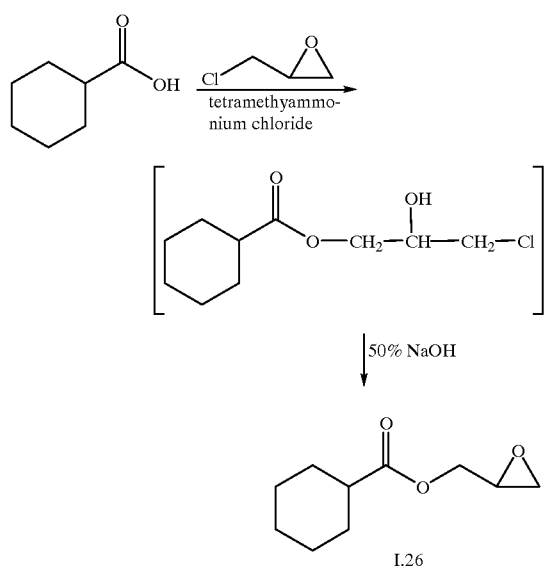

Analyses:

Appearance: colourless liquid, boiling point: 63° C./0.1 mm Hg $^1$H-NMR ($CDCl_3$, 300 MHz): The spectrum agrees with that expected of the product.

Empirical formula: $C_{10}H_{16}O_3$, molecular weight: 184.24 g/mol

Elemental analysis:

|   | calculated | found |
| --- | --- | --- |
| C | 65.19% | 64.89% |
| H | 8.75% | 8.89% |
| epoxy content | 5.43 mol/kg | 5.35 mol/kg |

EXAMPLE IV.8

39.8 g (0.1 mol) of 2-(2,4-dihydroxyphenyl)-4,6-(2,4-dimethylphenyl)-1,3,5-triazine, 26.4 g (0.11 mol) of cyclododecylglycidyl ether and 3.7 g (0.01 mol) of ethyltriphenylphosphonium bromide are suspended in 200 ml of xylene isomeric mixture. The mixture is then heated under reflux for 16 hours and subsequently cooled to room temperature. The solvent is evaporated off and the residue that remains is chromatographed over silica gel with toluene/ethyl acetate [95:5]. Evaporation of the solvent yields 37 g (58% of the theoretical yield) of a light-yellow product.

Analyses:

Appearance: light-yellow solid, melting point: 106–108° C.

$^1$H-NMR ($CDCl_3$, 300 MHz): The spectrum agrees with that expected of the product.

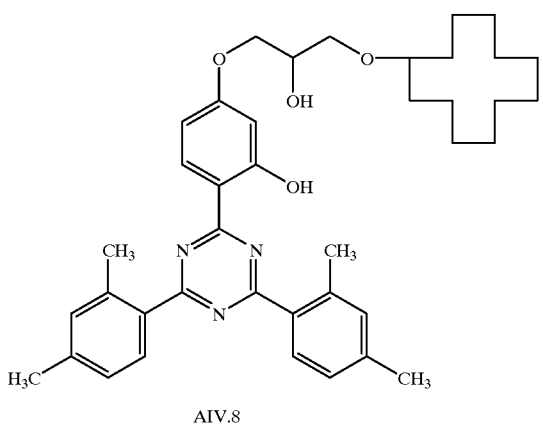

AIV.8

Empirical formula: $C_{40}H_{51}N_3O_4$, molecular weight: 637.86 g/mol
Elemental Analysis:

|   | calculated | found |
|---|---|---|
| C | 75.32% | 75.02% |
| H | 8.06% | 8.08% |
| N | 6.59% | 6.55% |

EXAMPLE V.8

49.36 g (0.1 mol) of 2-(2,4-dihydroxyphenyl)-4,6-(4-phenyl-phenyl)-1,3,5-triazine [for preparation see compound 115 in Example 15 in WO 96/28431], 26.4 g (0.11 mol) of cyclododecylglycidyl ether and 3.7 g (0.01 mol) of ethyltriphenylphosphonium bromide are suspended in 400 ml of xylene isomeric mixture. The mixture is heated under reflux for 24 hours and then cooled to room temperature. The solvent is evaporated off and the residue that remains is chromatographed over silica gel with toluene/ethyl acetate [95:5]. Evaporation of the solvent yields 47.5 g (64.7% of the theoretical yield) of a light-yellow product.

Analyses:
Appearance: light-yellow solid, melting point: 156–162° C.
$^1$H-NMR (CDCl$_3$, 300 MHz): The spectrum agrees with that expected of the product.

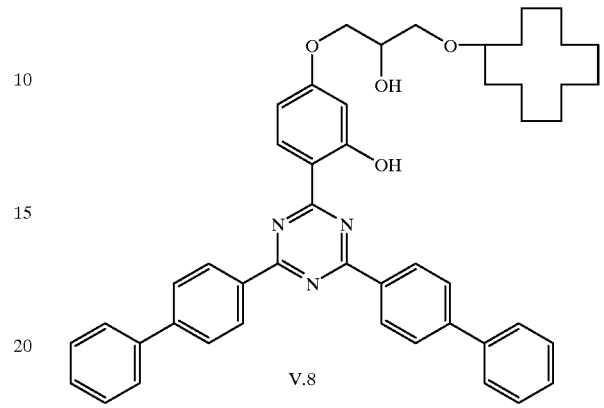

V.8

Empirical formula: $C_{48}H_{51}N_3O_4$, molecular weight: 733.48 g/mol
Elemental analysis:

|   | calculated | found |
|---|---|---|
| C | 78.55% | 78.28% |
| H | 7.00% | 6.88% |
| N | 5.73% | 5.60% |

Using a procedure in accordance with the process described under Example IV/V.8 and using as starting compounds the corresponding hydroxyphenyl-s-triazines of formula II, III or IV and the epoxides of formula I there are obtained compounds AI.1 to AIV.26 according to the invention. The radicals Z [=—(T)$_q$—R] are defined in Table 1.

I.1-I.26

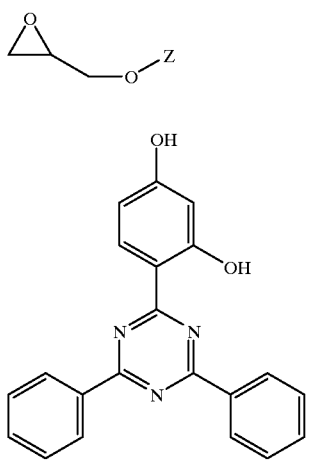

II

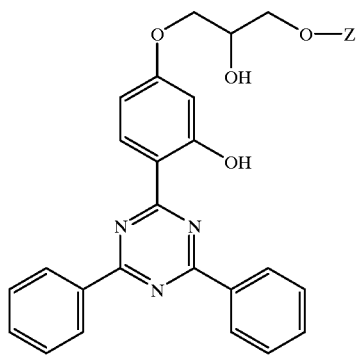
AII.1-AII.15 and AII.26
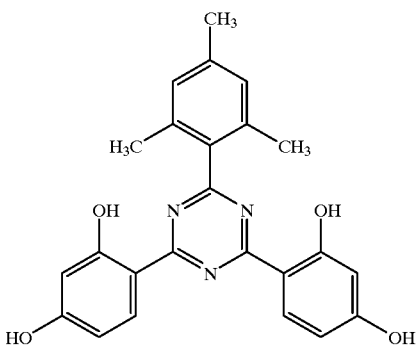
III
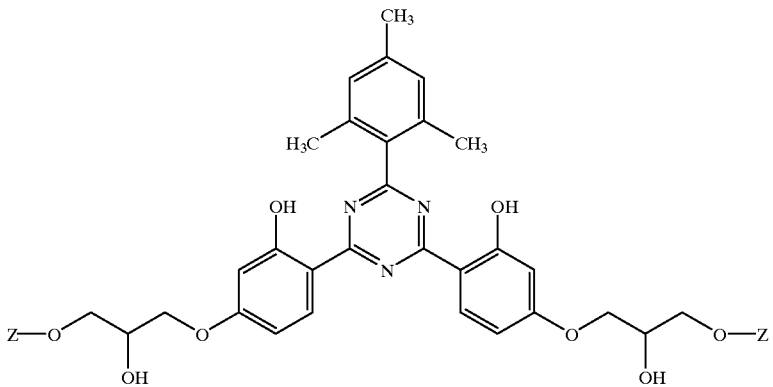
AIII.1-AIII.26
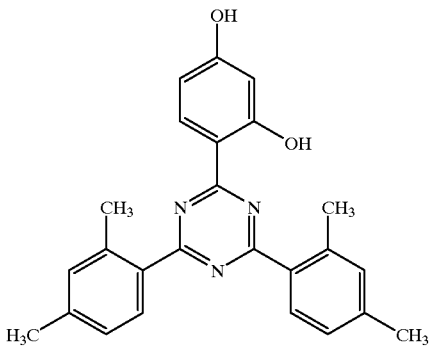
IV -continued
AIV.3-AIV.26
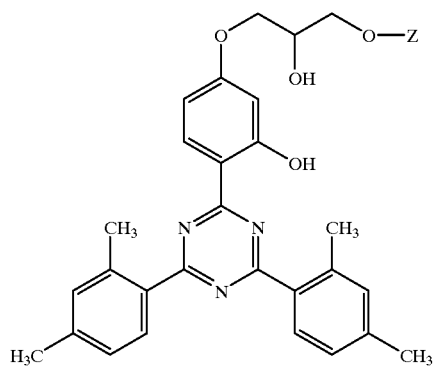
TABLE 1
Definition of Z
| # | Z | # | Z |
|---|---|---|---|
| 1 | PhCH₂— | 14 | 4-methylcyclohexyl-CH— |
| 2 | PhCH(CH₃)— | 15 | methylcyclohexyl-CH— (iso. mixture) |
| 3 | PhCH(CH₂CH₃)— | 16 | 2-tert-butylcyclohexyl-CH— |
| 4 | 4-CH₃O-C₆H₄-CH₂— | 17 | 4-tert-butylcyclohexyl-CH— |
| 5 | PhCH₂CH₂— | 18 | cyclohexyl-CH₂— |
| 6 | PhCH(CH₃)CH₂— | 19 | cyclohexyl-CH₂— |

TABLE 1-continued

Definition of Z

| # | Z | # | Z |
|---|---|---|---|
| 7 | 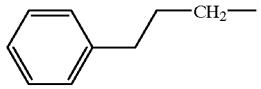 | 20 | 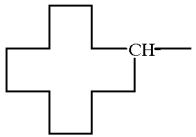 |
| 8 | 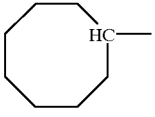 | 21 | 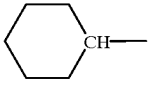 |
| 9 | 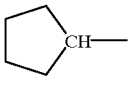 | 22 | 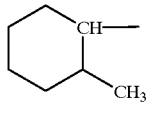 |
| 10 | 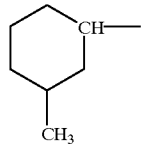 | 23 | 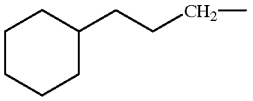 |
| 11 |  | 24 | 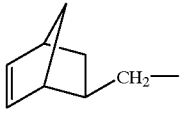 |
| 12 | 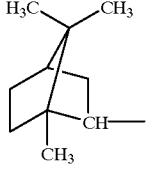 | 25 | 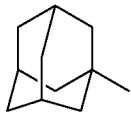 |
| 13 | 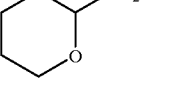 | 26 | 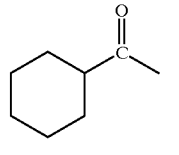 |

TABLE 2

| Compound | Appearance | Melting point in °C. | Empirical formula | Molecular weight in g/mol | % C calculated found | % H calculated found | % N calculated found | UV spectrum (in CHCl₃) $\epsilon_{max}1$ nm | | $\epsilon_{max}2$ nm | |
|---|---|---|---|---|---|---|---|---|---|---|---|
| AII.1 | light-yellow powder | 151–153 | $C_{31}H_{27}N_3O_4$ | 505.58 | 73.65 73.66 | 5.38 5.45 | 8.31 8.19 | 278 | 45 100 | 340 | 21 400 |
| AII.2 | light-yellow powder | 132.5–135 | $C_{32}H_{29}N_3O_4$ | 519.60 | 73.97 73.69 | 5.63 5.65 | 8.09 8.09 | 278 | 45 100 | 340 | 21 600 |
| AII.3 | light-yellow powder | 124–126 | $C_{33}H_{31}N_3O_4$ | 533.63 | 74.28 74.28 | 5.86 5.85 | 7.87 7.81 | 277 | 44 800 | 340 | 21 500 |
| AII.4 | light-yellow | 152–154 | $C_{32}H_{29}N_3O_5$ | 535.60 | 71.76 | 5.46 | 7.85 | 277 | 46 000 | 340 | 21 200 |

TABLE 2-continued

| Compound | Appearance | Melting point in °C. | Empirical formula | Molecular weight in g/mol | % C calculated found | % H | % N | UV spectrum (in CHCl₃) $\epsilon_{max}1$ nm | | $\epsilon_{max}2$ nm | |
|---|---|---|---|---|---|---|---|---|---|---|---|
| | powder | | | | 71.85 | 5.38 | 7.89 | | | | |
| AII.5 | light-yellow powder | 141–141.5 | $C_{32}H_{29}N_3O_4$ | 519.60 | 73.97 73.89 | 5.63 5.64 | 8.09 8.09 | 278 | 43 700 | 340 | 20 500 |
| AII.7 | light-yellow powder | 119–121 | $C_{36}H_{43}N_3O_4$ | 533.63 | 74.28 74.27 | 5.86 5.83 | 7.87 7.84 | 278 | 45 200 | 340 | 21 400 |
| AII.8 | light-yellow powder | 132–134 | $C_{30}H_{31}N_3O_4$ | 581.76 | 74.33 74.42 | 7.45 7.43 | 7.22 7.17 | 277 | 43 000 | 340 | 20 700 |
| AII.10 | light-yellow powder | 140–142 | $C_{31}H_{27}N_3O_4$ | 497.60 | 72.41 72.25 | 6.28 6.32 | 8.44 8.31 | 277 | 44 700 | 340 | 21 400 |
| AII.11 | light-yellow powder | 168–170 | $C_{29}H_{29}N_3O_4$ | 483.57 | 72.03 71.96 | 6.05 6.10 | 8.69 8.45 | 278 | 45 300 | 340 | 21 900 |
| AII.15 | light-yellow powder | 138–140 | $C_{31}H_{33}N_3O_4$ | 511.63 | 72.78 72.35 | 6.50 6.39 | 8.21 8.52 | 278 | 44 100 | 341 | 21 400 |
| AII.26 | light-yellow powder | 149[1] | $C_{31}H_{31}N_3O_5$ | 525.61 | 70.84 70.45 | 5.94 6.10 | 7.99 7.42 | 274 | 43 240 | 340 | 21 420 |
| AIII.1 | yellow powder | 65.9[1] | $C_{44}H_{45}N_3O_8$ | 743.86 | 71.05 70.68 | 6.09 6.08 | 5.65 5.68 | 352 | 42 900 | 299 | 33 780 |
| AIII.2 | yellow solid | 46.5 and 109[1] | $C_{46}H_{49}N_3O_8$ | 771.92 | 71.58 70.29 | 6.40 6.55 | 5.44 5.00 | 353 | 43 090 | 299 | 33 150 |
| AIII.3 | orange-coloured resin | −1.7[2] | $C_{48}H_{53}N_3O_8$ | 799.97 | 72.07 71.92 | 6.68 7.03 | 5.25 4.33 | 352 | 37 280 | 299 | 29 790 |
| AIII.4 | yellow powder | 155.3 and 166.7[1] | $C_{46}H_{49}N_3O_{10}$ | 803.92 | 68.73 68.95 | 6.14 6.20 | 5.23 5.01 | 353 | 43 530 | 299 | 33 200 |
| AIII.5 | yellow resin | 11.6[2] | $C_{48}H_{49}N_3O_8$ | 771.92 | 71.58 71.55 | 6.40 6.52 | 5.44 5.18 | 352 | 42 150 | 299 | 33 060 |
| AIII.6 | orange-coloured resin | −5.1[2] | $C_{48}H_{53}N_3O_8$ | 799.97 | 72.07 72.35 | 6.68 7.05 | 5.25 4.37 | 353 | 39 420 | 299 | 30 650 |
| AIII.7 | orange-coloured resin | 4.0[2] | $C_{48}H_{53}N_3O_8$ | 799.97 | 72.07 72.16 | 6.68 6.77 | 5.25 4.66 | 352 | 40 240 | 299 | 31 350 |
| AIII8 | orange-coloured resin | 31.9[1),2)] | $C_{54}H_{77}N_3O_8$ | 896.23 | 72.37 72.30 | 8.66 8.65 | 4.69 4.57 | 352 | 38 435 | 299 | 30 632 |
| AIII.9 | yellow solid | 148[1] | $C_{46}H_{61}N_3O_8$ | 784.01 | 70.47 70.20 | 7.84 8.05 | 5.36 5.14 | 353 | 41 250 | 300 | 31 550 |
| AIII.10 | yellow solid | 188–191 | $C_{42}H_{53}N_3O_8$ | 727.90 | 69.30 69.28 | 7.34 7.41 | 5.77 5.85 | 353 | 44 530 | 299 | 34 370 |
| AIII.11 | yellow solid | 144–151 | $C_{40}H_{49}N_3O_8$ | 699.85 | 68.65 68.84 | 7.06 7.05 | 6.00 5.77 | 351 | 38 270 | 298 | 31 690 |
| AIII.12 | orange-yellow solid | 52.8[1),2)] | $C_{44}H_{57}N_3O_8$ | 755.96 | 69.91 70.01 | 7.60 7.75 | 5.56 5.32 | 353 | 44 770 | 299 | 34 250 |
| AIII.13 | yellow solid | 56.2[1),2)] | $C_{44}H_{57}N_3O_8$ | 755.96 | 69.91 69.06 | 7.60 7.57 | 5.56 5.49 | 352 | 43 950 | 299 | 34 970 |
| AIII.14 | yellow solid | 124.7[1] | $C_{44}H_{57}N_3O_8$ | 755.96 | 69.91 69.23 | 7.60 7.51 | 5.56 5.49 | 352 | 43 435 | 299 | 33 880 |
| AIII.15 | yellow resinous solid | 17.4[1] | $C_{44}H_{57}N_3O_8$ | 755.96 | 69.91 69.94 | 7.60 7.96 | 5.56 5.13 | 352 | 40 110 | 299 | 31 830 |
| AIII.16 | yellow resin | 53.7[1),2)] | $C_{50}H_{69}N_3O_8$ | 840.12 | 71.48 71.06 | 8.28 8.31 | 5.00 4.31 | 353 | 42 140 | 298 | 33 710 |
| AIII.17 | yellow solid | 57.8[1),2)] | $C_{50}H_{69}N_3O_8$ | 840.12 | 71.48 71.53 | 8.28 8.38 | 5.00 4.34 | 353 | 43 380 | 298 | 35 520 |
| AIII.18 | orange-yellow solid | 61.8[1),2)] | $C_{44}H_{57}N_3O_8$ | 755.96 | 69.91 69.58 | 7.60 7.92 | 5.56 4.92 | 351 | 37 105 | 299 | 29 720 |
| AIII.19 | orange-coloured resin | 16.5[1),2)] | $C_{46}H_{61}N_3O_8$ | 784.01 | 70.47 70.23 | 7.84 7.87 | 5.36 4.91 | 352 | 39 480 | 299 | 31 110 |
| AIII.20 | yellow solid | 67.8[1] | $C_{48}H_{65}N_3O_8$ | 812.07 | 70.99 71.05 | 8.07 8.31 | 5.17 4.90 | 353 | 42 900 | 299 | 31 780 |
| AIII.21 | yellow solid | 163.1[1] | $C_{46}H_{57}N_3O_8$ | 779.98 | 70.84 70.54 | 7.37 7.60 | 5.39 4.98 | 353 | 44 670 | 299 | 34 730 |
| AIII.22 | yellow powder | 161.6[1] | $C_{46}H_{53}N_3O_8$ | 775.95 | 71.20 71.22 | 6.88 6.87 | 5.41 5.18 | 353 | 42 834 | 299 | 33 135 |
| AIII.23 | yellow solid | 57.0[1),2)] | $C_{50}H_{65}N_3O_8$ | 836.09 | 71.83 72.21 | 7.84 8.11 | 5.02 4.55 | 353 | 41 290 | 299 | 31 715 |
| AIII.25 | yellow solid | 145.4[1] | $C_{42}H_{53}N_3O_{10}$ | 759.91 | 66.38 66.24 | 7.03 7.08 | 5.53 5.33 | 353 | 43 250 | 299 | 32 550 |
| AIII.26 | light-yellow solid | 162[1] | $C_{44}H_{53}N_3O_{10}$ | 783.93 | 67.42 67.33 | 6.81 7.01 | 5.36 4.76 | 352 | 41 620 | 298 | 33 660 |
| AIV.3 | light-yellow solid | 113–115 | $C_{37}H_{39}N_3O_4$ | 589.74 | 75.36 75.27 | 6.67 6.69 | 7.13 6.45 | 336 | 21 100 | 291 | 42 560 |
| AIV.4 | light-yellow solid | 90–92 | $C_{36}H_{37}N_3O_5$ | 591.71 | 73.08 73.81 | 6.30 6.48 | 7.10 6.21 | 337 | 20 165 | 290 | 40 540 |
| AIV.6 | light-yellow solid | 78–79 | $C_{37}H_{39}N_3O_4$ | 589.74 | 75.36 75.08 | 6.67 6.59 | 7.13 6.85 | 337 | 21 840 | 291 | 44 210 |

TABLE 2-continued

| Com-pound | Appearance | Melting point in °C. | Empirical formula | Molecular weight in g/mol | % C calculated found | % H | % N | UV spectrum (in CHCl$_3$) $\epsilon_{max}$1 nm | | $\epsilon_{max}$2 nm | |
|---|---|---|---|---|---|---|---|---|---|---|---|
| AIV.7 | light-yellow solid | 85–87 | C$_{37}$H$_{39}$N$_3$O$_4$ | 589.74 | 75.36 75.14 | 6.67 6.61 | 7.13 7.12 | 337 | 21 960 | 291 | 45 017 |
| AIV.12 | light-yellow solid | 69–71 | C$_{35}$H$_{41}$N$_3$O$_4$ | 567.73 | 74.05 73.80 | 7.28 7.27 | 7.40 7.03 | 336 | 22 740 | 291 | 45 540 |
| AIV.13 | light-yellow solid | 89–91 | C$_{35}$H$_{41}$N$_3$O$_4$ | 567.73 | 74.05 73.98 | 7.28 7.42 | 7.40 7.35 | 336 | 23 170 | 291 | 46 560 |
| AIV.14 | light-yellow solid | 76–77 | C$_{35}$H$_{41}$N$_3$O$_4$ | 567.73 | 74.05 73.07 | 7.28 6.96 | 7.40 7.19 | 336 | 22 940 | 291 | 46 350 |
| AIV.16 | light-yellow solid | 106–107 | C$_{38}$H$_{47}$N$_3$O$_4$ | 609.81 | 74.85 74.91 | 7.77 7.81 | 6.89 6.76 | 337 | 22 970 | 291 | 45 860 |
| AIV.17 | light-yellow solid | 109–110 | C$_{38}$H$_{47}$N$_3$O$_4$ | 609.81 | 74.85 74.58 | 7.77 7.86 | 6.89 6.40 | 336 | 22 480 | 291 | 44 970 |
| AIV.20 | | | C$_{37}$H$_{45}$N$_3$O$_4$ | 595.78 | 74.59 73.67 | 7.61 7.84 | 7.05 7.01 | 337 | 22 230 | 290 | 45 630 |
| AIV.21 | light-yellow solid | 59–61 | C$_{36}$H$_{41}$N$_3$O$_4$ | 579.74 | 74.58 74.20 | 7.13 7.14 | 7.25 6.93 | 336 | 22 220 | 291 | 44 990 |
| AIV.22 | light-yellow solid | 49–51 | C$_{36}$H$_{39}$N$_3$O$_4$ | 577.72 | 74.84 74.65 | 6.80 6.85 | 7.27 7.33 | 337 | 22 410 | 291 | 45 670 |
| AIV.25 | light-yellow solid | 69–71 | C$_{34}$H$_{39}$N$_3$O$_5$ | 569.70 | 71.68 71.09 | 6.90 6.81 | 7.38 7.09 | 337 | 22 630 | 291 | 44 905 |
| AIV.26 | light-yellow solid | 140[1] | C$_{35}$H$_{39}$N$_3$O$_5$ | 581.72 | 72.27 72.10 | 6.76 6.77 | 7.22 7.12 | 336 | 23 910 | 288 | 47 260 |

[1]DSC
[2]Tg
AII.26 and AIII.1–AIV.26 (in AcOEt)
$^1$H-NMR (CDCl$_3$ 300 MHz): All spectra of compounds AII.1 to AIV.26 agree with the expected spectra of the products.

EXAMPLE 1

Light Stabilisation of Polypropylene Fibres 2.5 g of the stabiliser according to the invention from Example IV.8 together with 1 g of tris(2,4-di-tert-butylphenyl)phosphite, 1 g of calcium monoethyl-3,5-di-tert-butyl-4-hydroxybenzyl phosphonate, 1 g of calcium stearate and 2.5 g of TiO$_2$ (Kronos RN 57) are mixed in a turbomixer with 1000 g of polypropylene powder (melting index 12 g/10 min, measured at 230° C./2.16 kg). The mixtures are extruded at 200–230° C. to form granules which are then processed to form fibres with the aid of a Pilot system (Leonard; Sumirago/VA, Italy) under the following conditions:

| | |
|---|---|
| extruder temperature | 190–230° C. |
| head temperature | 255–260° C. |
| extension ratio | 1:3.5 |
| extension temperature | 100° C. |
| fibres | 10 den |

The fibres so produced are illuminated in accordance with ASTM D 2565-85 in front of a white background in a Weather-O-Meter® type 65 WR (Atlas Corp.) at a black standard temperature of 63° C. After various illumination periods, the remaining tensile strength of the samples is measured. The measured values are used to calculate the illumination time T$_{50}$ after which the tensile strength of the samples has been reduced by half.

For comparison purposes, fibres are prepared without stabiliser according to the invention, but otherwise under the same conditions, and are tested.

The fibres stabilised according to the invention exhibit excellent strength retention.

EXAMPLE 2

Stabilisation of a Two-layer Surface Coating

The stabilisers according to the invention are incorporated into 30 g of Solvesso® 100 and tested in a clear lacquer having the following composition:

| | |
|---|---|
| Synthacryl ® SC 303[1] | 27.51 g |
| Synthacryl ® SC 370[2] | 23.34 g |
| Maprenal ® MF 650[3] | 27.29 g |
| butyl acetate/butanol (37/8) | 4.33 g |
| isobutanol | 4.87 g |
| Solvesso ® 150[4] | 2.72 g |
| white spirits K-30[5] | 8.74 g |
| flow auxiliary Baysil ® MA[6] | 1.20 g |
| | 100.00 g |

[1]acrylate resin, Hoechst AG; 65% solution in xylene/butanol 26:9
[2]acrylate resin, Hoechst AG; 75% solution in Solvesso ® 100[4]
[3]melamine resin, Hoechst AG; 55% solution in isobutanol
[4]manufacturer: ESSO
[5]manufacturer: Shell
[6]1% in Solvesso ® 150; manufacturer: Bayer AG 1.5% of stabilisers according to the invention, based on the solids content of the lacquer, are added to the clear lacquer. To some further lacquer samples there are added, in addition to the compounds according to the invention, 1% of the compound TINUVIN® 123

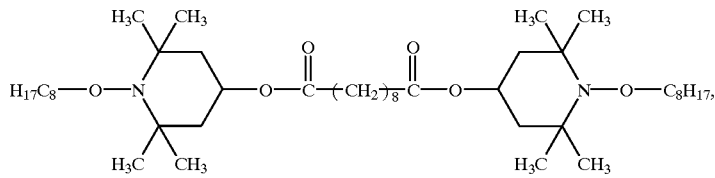

based on the solids content of the lacquer. A clear lacquer containing no light stabiliser is used as comparison.

The clear lacquer is diluted to a sprayable consistency with Solvesso® 100 and applied by spraying to a pre-prepared aluminium sheet (coil coat, filler, silver-metallic or light-green-metallic base lacquer) and stoved at 130° C. for 30 minutes, resulting in a dry film thickness of 40–50 mm clear lacquer.

The samples are then subjected to weathering in a UVCON® weathering apparatus supplied by Atlas Corp. (UVB-313 lamps) with a cycle of 4 hours' UV irradiation at 60° C. and 4 hours' condensation at 50° C.

The samples are examined for cracks at regular intervals.

TABLE 1

20° * gloss defined as in DIN 67530 after 0, 800, 1200, 2000 and 2400 hours' weathering in a ® UVCON (UVB-313) (light-green metallic base lacquer)

| Stabiliser | 0 h | 800 h | 1200 h | 2000 h | 2400 h |
|---|---|---|---|---|---|
| without | 86 | 53 | 18 | ** | |
| 1.5% AII.2 | 87 | 87 | 87 | 87 | 75*** |
| 1.5% AII.18 | 86 | 87 | 86 | 87 | 84*** |

*high values represent a good stabilising action
**crack formation after 1200 hours
***crack formation after 2400 hours

TABLE 2

20° * gloss defined as in DIN 67530 after 0, 1600, 4400, 5600 and 6000 hours' weathering in a ® UVCON (UVB-313) (silver-metallic base lacquer)

| Stabiliser | 0 h | 1600 h | 4400 h | 5600 h | 6000 h |
|---|---|---|---|---|---|
| without | 92 | 16 | ** | | |
| 1.5% AIII.6 + 1% TINUVIN ® 123 | 92 | 91 | 88 | 87 | 80 |
| 1.5% AIII.12 + 1% TINUVIN ® 123 | 92 | 89 | 90 | 88 | 87 |
| 1.5% AIII.13 + 1% TINUVIN ® 123 | 92 | 94 | 90 | 89 | 85 |
| 1.5% AIII.17 + 1% TINUVIN ® 123 | 92 | 87 | 86 | 84 | 73 |
| 1.5% AIII.20 + 1% TINUVIN ® 123 | 92 | 92 | 90 | 88 | 83 |

*high values represent a good stabilising action
**crack formation after 1600 hours

TABLE 3

20° * gloss defined as in DIN 67530 after 0, 800, 1200, 1600 and 2000 hours' weathering in a ® UVCON (UVB-313) (silver-metallic base lacquer)

| Stabiliser | 0 h | 800 h | 1200 h | 1600 h | 2000 h |
|---|---|---|---|---|---|
| without | 86 | 46 | 9 | 9** | |
| 1.5% AIV.8 | 85 | 88 | 87 | 85 | 43*** |

*high values represent a good stabilising action
**crack formation after 1200 hours
***crack formation after 2000 hours

TABLE 4

20° * gloss defined as in DIN 67530 after 0, 1200, 4000, 5600 and 6000 hours' weathering in a ® UVCON (UVB-313) (light-green metallic base lacquer)

| Stabiliser | 0 h | 1200 h | 4000 h | 5600 h | 6000 h |
|---|---|---|---|---|---|
| without | 86 | 29 | ** | | |
| 1.5% AIV.14 + 1% TINUVIN ® 123 | 88 | 88 | 88 | 82 | 75*** |
| 1.5% AIV.17 + 1% TINUVIN ® 123 | 86 | 87 | 86 | 83 | 72*** |
| 1.5% AIV.20 + 1% TINUVIN ® 123 | 87 | 89 | 87 | 84 | 77**** |
| 1.5% AIV.21 + 1% TINUVIN ® 123 | 86 | 89 | 88 | 84 | 75**** |
| 1.5% AIV.22 + 1% TINUVIN ® 123 | 88 | 89 | 88 | 87 | 85***** |

*high values represent a good stabilising action
**crack formation after 1600 hours
***crack formation after 5600 hours
****crack formation after 6000 hours
*****crack formation after 6800 hours The samples comprising the stabilisers according to the invention have a high degree of resistance to crack formation.

EXAMPLE 3

Stabilisation of a Photographic Material 0.087 g of the yellow coupler of formula

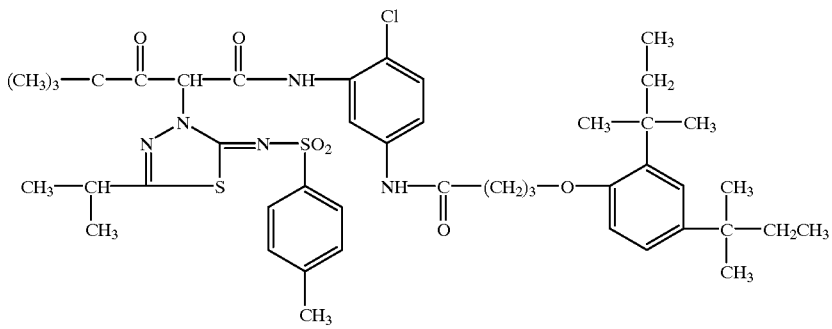

are dissolved in 2.0 ml of a solution of the stabiliser according to the invention from Example IV.8 in ethyl acetate (2.25 g/100 ml). To 1.0 ml of that solution there are added 9.0 ml of a 2.3% aqueous gelatin solution, which has been adjusted to a pH value of 6.5 and contains 1.744 g/l of the wetting agent of formula

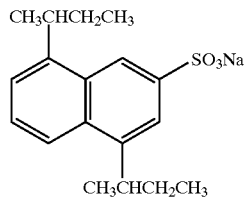

To 5.0 ml of the coupler emulsion so obtained there are added 2 ml of a silver bromide emulsion having a silver content of 6.0 g/l, and 1.0 ml of a 0.7% aqueous solution of the hardener of formula

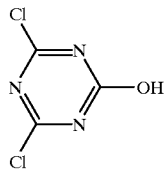

and the mixture is poured onto a 13×18 cm piece of plastics-coated paper. After a curing time of 7 days, the samples are illuminated behind a silver step wedge at 125 Lux•s and then processed using the Kodak Ektaprint 2® process.

The resulting yellow wedges are irradiated in an Atlas Weather-Ometer® with a 2500 W xenon lamp behind a UV filter (Kodak 2C) with a total of 60 kJoule/cm$^2$.

A sample without stabiliser is used as standard.

The loss of colour density occurring during the irradiation at the absorption maximum of the yellow dye is measured using a Densitometer TR 924 A supplied by Macbeth.

The light-stabilising effect can be seen from the loss of colour density. The smaller the loss of density, the higher the light-stabilising effect.

The stabiliser according to the invention exhibits a good light-stabilising action.

EXAMPLE 4

Stabilisation of Polypropylene Strips 1.0 g of the stabiliser according to the invention from Example IV.8 together with 1 g of tris(2,4-di-tert-butylphenyl)phosphite, 0.5 g of pentaerythrityl-tetrakis(3-[3',5'-di-tert-butyl4'-hydroxyphenyl]-propionate) and 1 g of calcium stearate is mixed in a turbomixer with 1000 g of polypropylene powder (STATOILMF; melting index 4.0 g/10 min., measured at 230° C./2.16 kg).

The mixtures are extruded at 200–230° C. to form granules which are then processed to form 2.5 mm wide extended strips of 50 mm thickness with the aid of a Pilot system (Leonard; Sumirago/VA, Italy) under the following conditions:

| | |
|---|---|
| extruder temperature | 210–230° C. |
| head temperature | 240–260° C. |
| extension ratio | 1:6 |
| extension temperature | 110° C. |

The strips so produced are illuminated in accordance with ASTM D 2565-85 in front of a white background in a Weather-O-Meter® type 65 WR (Atlas Corp.) at a black standard temperature of 63° C. After various illumination periods, the remaining tensile strength of the samples is measured. The measured values are used to calculate the illumination time $T_{50}$ after which the tensile strength of the samples has been reduced by half.

For comparison purposes, strips are prepared without the stabiliser according to the invention, but otherwise under the same conditions, and are tested.

The sample stabilised according to the invention exhibits excellent strength retention.

What is claimed is:

1. A compound of formula A

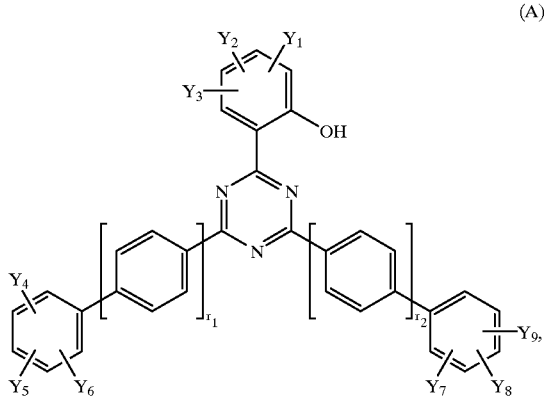

wherein $r_1$ and $r_2$ are each independently of the other 0 or 1;

$Y_1$ to $Y_9$ are each independently of the others —H, —OH, $C_1$–$C_{20}$alkyl, $C_4$–$C_{12}$cycloalkyl, $C_2$–$C_{20}$alkenyl, $C_1$–$C_{20}$alkoxy, $C_4$–$C_{12}$cycloalkoxy, $C_2$–$C_{20}$alkenyloxy, $C_7$–$C_{20}$aralkyl, halogen, —C≡N, $C_1$–$C_5$haloalkyl, —$SO_2R'$, —$SO_3H$, —$SO_3M$, wherein M is an alkali metal, —COOR', —CONHR', —CONR'R", —OCOOR', —OCOR', —OCONHR', (meth)acrylamino, (meth)acryloxy, $C_6$–$C_{12}$aryl; $C_6$–$C_{12}$aryl substituted by $C_1$–$C_{12}$alkyl, $C_1$–$C_{12}$alkoxy, CN and/or by halogen; pyridinyl, pyrimidinyl, triazinyl, pyrrolyl, furanyl, thiophenyl, quinolinyl; pyridinyl, pyrimidinyl, triazinyl, pyrrolyl, furanyl, thiophenyl, quinolinyl substituted by $C_1$–$C_{12}$alkyl, $C_1$–$C_{12}$alkoxy, CN and/or by halogen; or Q of formula I, and at least one substituent $Y_1$ to $Y_9$ must be Q

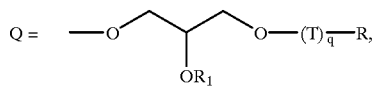

(I)

wherein
q is 0 or 1, and
$R_1$ is —H, $C_1$–$C_{20}$alkyl, $C_4$–$C_{12}$cycloalkyl, —COR', —COOR' or —CONHR', and
T is $C_1$–$C_{20}$alkylene; $C_4$–$C_{12}$cycloalkylene; $C_1$–$C_{20}$alkylene-O—; $C_2$–$C_{50}$alkylene that is interrupted one or more oxygen atoms and/or substituted by one or more hydroxy groups; —CO—; —$SO_2$—; phenylene; phenylene substituted by $C_1$–$C_{12}$alkyl, $C_1$–$C_{12}$alkoxy, CN and/or by halogen; biphenylene; or biphenylene substituted by $C_1$–$C_{12}$alkyl, $C_1$–$C_{12}$alkoxy, CN and/or by halogen, it being possible for T, in place of hydrogen, to be substituted by one or more substituents $R_x$ that are independent of one another, and
R is $C_4$–$C_{12}$cycloalkyl, $C_4$–$C_{12}$cycloalkenyl, $C_6$–$C_{15}$bicycloalkyl, $C_6$–$C_{15}$bicycloalkenyl or $C_6$–$C_{15}$tricycloalkyl, each of which may be interrupted by one or more oxygen atoms, or is naphthyl or biphenyl and, in the case where q is 1, additionally includes phenyl, it being possible for R, in place of hydrogen, to be substituted by one or more substituents $R_x$ that are independent of one another, and
$R_x$ is $C_1$–$C_{20}$akyl, $C_2$–$C_{20}$alkenyl, $C_4$–$C_{12}$cycloalkyl, $C_1$–$C_{20}$alkoxy, $C_4$–$C_{12}$cycloalkoxy, hydroxy, halogen, $C_1$–$C_5$haloalkyl, —COOR', —CONHR', —CONR'R", —OCOR', —OCOOR', —OCONHR', —$NH_2$, —NHR', —NR'R", —NHCOR', —NR"COR', —NH(meth)acryl, —O(meth)acryl, —CN, =O, =NR'; $C_6$–$C_{12}$aryl, or $C_6$–$C_{12}$aryl substituted by $C_1$–$C_{12}$alkyl, $C_1$–$C_{12}$alkoxy, CN and/or by halogen; and R' and R" are each independently of the other —H; $C_1$–$C_{20}$allyl; $C_4$–$C_{12}$cycloalkyl; $C_6$–$C_{12}$aryl; $C_6$–$C_{12}$aryl substituted by $C_1$–$C_{12}$alkyl, $C_1$–$C_{12}$alkoxy, CN and/or by halogen; pyridinyl, pyrimidinyl, triazinyl, pyrrolyl, furanyl, thiophenyl, quinolinyl; or pyridinyl, pyrimidinyl, triazinyl, pyrrolyl, furanyl, thiophenyl, quinolinyl substituted by $C_1$–$C_{12}$alkyl, $C_1$–$C_{12}$alkoxy, CN and/or by halogen;

with the exception of the compound 2,4-bisphenyl-6-(4-[3-benzoyloxy-2-hydroxypropyloxy]-2-hydroxyphenyl)-1,3,5-triazine.

2. A compound according to claim 1 of formula A1

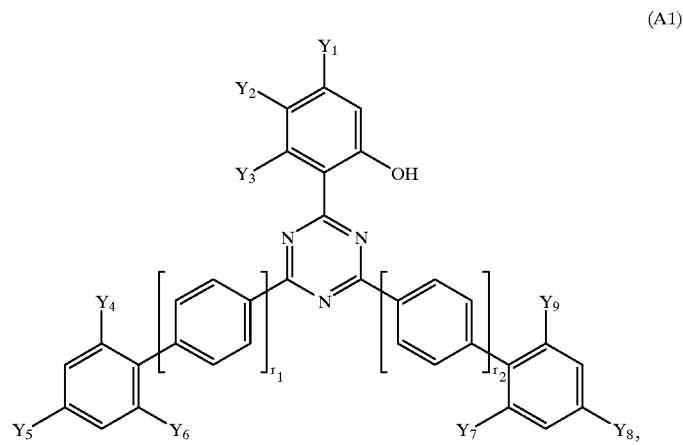

(A1)

wherein $r_1$ and $r_2$ and the substituents $Y_1$ to $Y_9$ are as defined in claim 1.

3. A compound according to claim 2, wherein
$Y_1$ is Q;
$Y_2$ is H, $C_1$–$C_{20}$alkyl, $C_5$–$C_{12}$cycloalkyl, $C_7$–$C_{20}$aralkyl, $C_1$–$C_5$haloalkyl or —$SO_2R'$;
$Y_3$ is H;
$Y_4$ to $Y_9$ are each independently of the others —H, —OH, $C_1$–$C_{20}$alkyl, $C_4$–$C_{12}$cycloalkyl, $C_2$–$C_{20}$alkenyl, $C_1$–$C_{20}$alkoxy, $C_4$–$C_{12}$cycloalkoxy, $C_2$–$C_{20}$alkenyloxy, $C_7$–$C_{20}$aralkyl, halogen, —C≡N, $C_1$–$C_5$haloalkyl, —$SO_2R'$, —$SO_3H$, —$SO_3M$, —COOR', —CONHR', —CONR'R", —OCOOR', —OCOR', —OCONHR', (meth)acrylamino, (meth)acryloxy, $C_6$–$C_{12}$aryl; $C_6$–$C_{12}$aryl substituted by $C_1$–$C_{12}$alkyl, $C_1$–$C_{12}$alkoxy, CN and/or by halogen; pyridinyl, pyrimidinyl, triazinyl, pyrrolyl, furanyl, thiophenyl, quinolinyl; or pyridinyl, pyrimidinyl, triazinyl, pyrrolyl, furanyl, thiophenyl, quinolinyl substituted by $C_1-C_{12}$alkyl, $C_1-C_{12}$alkoxy, CN and/or by halogen; and $Y_5$ and $Y_9$ additionally include Q; Q being a radical of formula (I)

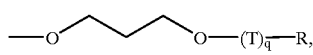
(I)

wherein q is 0 or 1, and $R_1$ is —H, $C_1-C_{20}$alkyl, $C_4-C_{12}$cycloalkyl, —COR', —COOR' or —CONHR';

T is $C_1-C_{20}$alkylene; $C_4-C_{12}$cycloalkylene; $C_1-C_{20}$alkylene-O—; $C_2-C_{50}$alkylene that is interrupted by O and/or substituted by OH; —CO—; —SO$_2$—; phenylene; or phenylene substituted by $C_1-C_{12}$alkyl, $C_1-C_{12}$alkoxy, CN and/or by halogen;

R is $C_4-C_{12}$cycloalkyl, $C_4-C_{12}$cycloalkenyl, $C_6-C_{15}$bicycloalky, $C_6-C_{15}$bicycloalkenyl or $C_6-C_{15}$tricycloalkyl, each of which may be interrupted by one or more oxygen atoms, or is naphthyl or biphenyl and, in the case where q is 1 and T is other than —CO—, additionally includes phenyl, it being possible for R in the said definitions to be substituted by $R_x$;

$R_x$ is $C_1-C_{12}$alkyl, $C_2-C_{20}$alkenyl, $C_1-C_4$alkoxy, hydroxy, halogen, $C_1-C_5$haloalkyl, —COOR', —CONHR', —CONR'R", —OCOR', —OCOOR', —OCONHR', —NH(meth)acryl, —O(meth)acryl, —CN, =O, =NR'; phenyl, or phenyl substituted by $C_1-C_{12}$alkyl, $C_1-C_{12}$alkoxy, CN and/or by halogen; and R' and R" are each independently of the other $C_1-C_{12}$alkyl, $C_5-C_{12}$cycloalkyl, phenyl, or phenyl substituted by $C_1-C_{12}$alkyl, $C_1-C_{12}$alkoxy, CN and/or by halogen.

4. A compound according to claim 3, wherein $r_1$ and $r_2$ are 0, and $Y_4$ and $Y_7$ are each independently of the other —H, —OH, $C_1-C_{12}$alkyl, $C_1-C_{12}$alkoxy, $C_2-C_{20}$alkenyloxy, halogen, $C_1-C_5$haloalkyl or (meth)acryloxy;

$Y_5$ and $Y_8$ are each independently of the other —H, —OH, $C_1-C_{20}$alkyl, $C_2-C_{20}$alkenyl, $C_1-C_{20}$-alkoxy, $C_4-C_{12}$cycloalkoxy, $C_3-C_{20}$alkenyloxy, $C_7-C_{20}$phenylalkyl, halogen, $C_1-C_5$haloalkyl, —SO$_2$R', —SO$_3$H, —SO$_3$M, —OCOOR', —OCOR', —OCONHR', (meth)acrylamino, (meth)acryloxy, phenyl; phenyl substituted by $C_1-C_{12}$alkyl, $C_1-C_{12}$alkoxy, CN and/or by halogen; or Q;

wherein in Q of formula (I)

$R_1$ is H;

T is $C_1-C_6$alkyl and

R is $C_4-C_{12}$cycloalkyl, $R_x$-substituted $C_4-C_{12}$cycloalkyl, phenyl, $R_x$-substituted phenyl, or $C_5-C_{12}$cycloalkenyl, $C_6-C_{15}$bicycloalkyl or $C_6-C_{15}$tricycloalkyl, each of which may be interrupted by one or more oxygen atoms and/or substituted by $R_x$;

$R_x$ is $C_1-C_4$alkyl or $C_1-C_4$alkoxy; and $Y_6$ and $Y_9$ are H or $C_1-C_{12}$alkyl.

5. A compound according to claim 1 of one of the formulae A2, A3, A4, A5, A6, A7 and A8

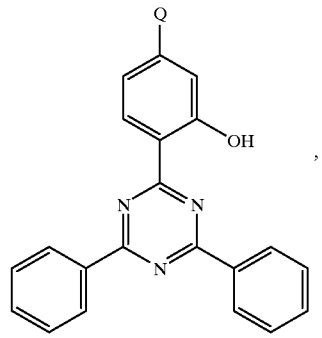
(A2)

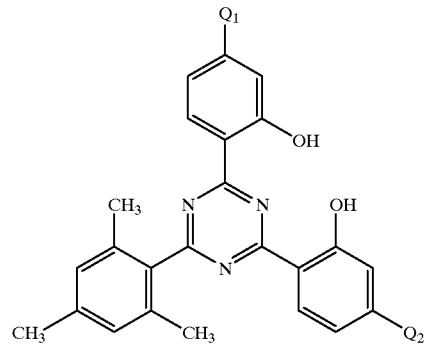
(A3)

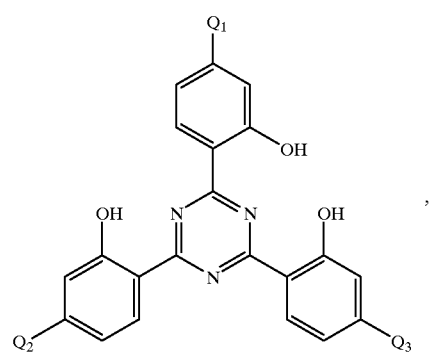
(A4)

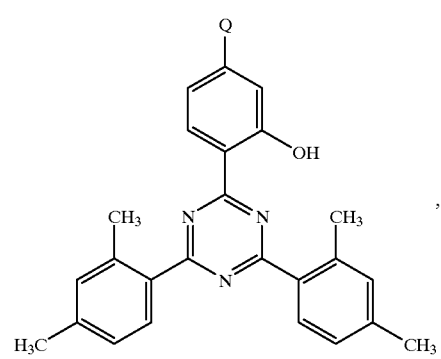
(A5)

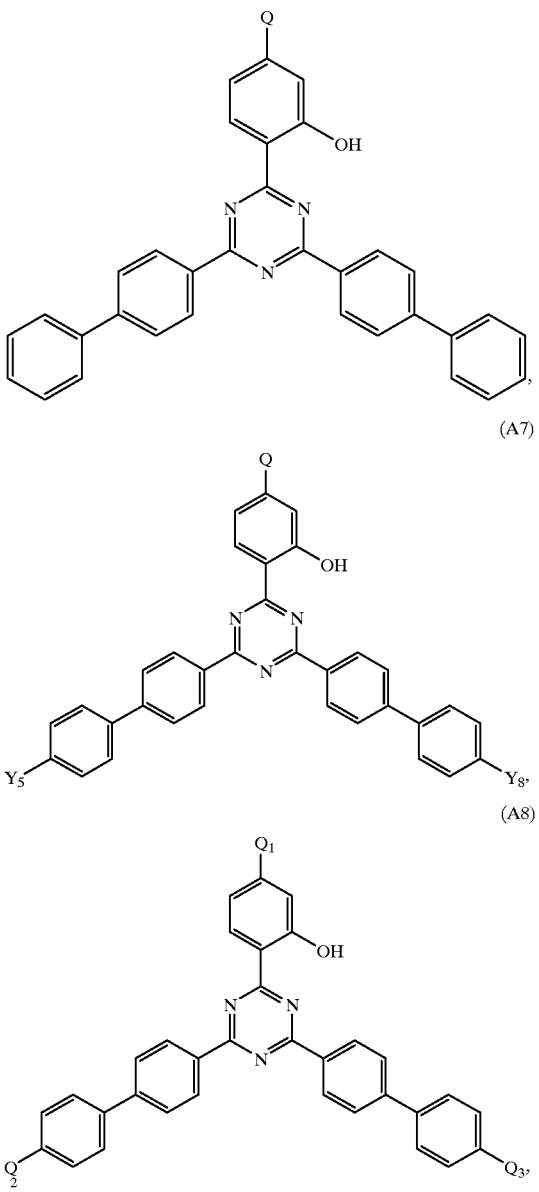

in which formulae $Y_5$ and $Y_8$ are each independently of the other —OH, $C_1$–$C_{20}$alkyl, $C_1$–$C_{20}$alkoxy, $C_4$–$C_{12}$cycloalkoxy, $C_3$–$C_{20}$alkenyloxy, $C_7$–$C_{20}$phenylalkyl, halogen, $C_1$–$C_5$haloalkyl, —$SO_2R'$, —$SO_3H$, —$SO_3M$, —OCOOR', —OCOR', —OCONHR', (meth)acrylamino or (meth)acryloxy and the substituents $Q_1$ to $Q_3$ include the meanings defined for Q.

6. A compound according to claim 5 of one of the formulae A2, A3, A4, A5, A6, A7 and A8, wherein $Q_1$, $Q_2$ and $Q_3$ are identical and $Y_5$ and $Y_8$ are identical.

7. A stabiliser mixture comprising
   (a) a compound of formula A according to claim 1 and
   (b) at least one 2,2,6,6-tetraalkylpiperidine derivative, or a salt thereof with any desired acid or a complex thereof with a metal.

8. A composition comprising
   1) an organic material susceptible to damage by light, oxygen and/or heat, and
   2) as stabiliser at least one compound according to claim 1.

9. A composition according to claim 8, wherein component 1) is an organic polymer.

10. A composition according to claim 8, wherein component 1) is a synthetic polymer.

11. A composition according to claim 8, wherein component 1) is a polyolefin or a surface-coating binder based on acrylic, alkyd, polyurethane, polyester or polyamide resin or correspondingly modified resins, a photographic material, a cosmetic or a sun cream.

12. A composition according to claim 8 comprising, in addition to components 1) and 2), further customary additives.

13. A composition according to claim 8 comprising from 0.01 to 10% by weight of component 2), based on the weight of the composition.

14. A method of stabilising organic material against damage by light, oxygen and/or heat, wherein a compound according to claim 1 is mixed with that material.

15. A polymer protected against damage by light, oxygen and/or heat in accordance with the method of claim 14.

16. A surface coating protected against damage by light, oxygen and/or heat in accordance with the method of claim 14.

17. A photographic material protected against damage by light, oxygen and/or heat in accordance with the method of claim 14.

* * * * *